US012662538B2

(12) United States Patent
Piwnica-Worms et al.

(10) Patent No.: US 12,662,538 B2
(45) Date of Patent: Jun. 23, 2026

(54) ANTI-B7-H3 MONOCLONAL ANTIBODY AND METHODS OF USE THEREOF

(71) Applicant: Board of Regents, The University of Texas System, Austin, TX (US)

(72) Inventors: David Piwnica-Worms, Houston, TX (US); Seth Gammon, Houston, TX (US); Federica Pisaneschi, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 899 days.

(21) Appl. No.: 17/777,946

(22) PCT Filed: Nov. 18, 2020

(86) PCT No.: PCT/US2020/061050
§ 371 (c)(1),
(2) Date: May 18, 2022

(87) PCT Pub. No.: WO2021/101991
PCT Pub. Date: May 27, 2021

(65) Prior Publication Data
US 2023/0014398 A1     Jan. 19, 2023

Related U.S. Application Data

(60) Provisional application No. 62/936,783, filed on Nov. 18, 2019.

(51) Int. Cl.
| | |
|---|---|
| *C07K 16/28* | (2006.01) |
| *A61K 51/10* | (2006.01) |
| *A61P 35/00* | (2006.01) |

(52) U.S. Cl.
CPC .......... *C07K 16/2827* (2013.01); *A61K 51/10* (2013.01); *A61P 35/00* (2018.01); *C07K 2317/24* (2013.01); *C07K 2317/31* (2013.01); *C07K 2317/55* (2013.01); *C07K 2317/622* (2013.01)

(58) Field of Classification Search
CPC ............ C07K 16/2827; C07K 2317/24; C07K 2317/31; C07K 2317/55; C07K 2317/622; C07K 2317/33; C07K 2317/92; C07K 2319/03; C07K 14/7051; C07K 2317/73; A61K 51/10; A61K 47/6811; A61K 47/6849; A61K 49/0041; A61K 49/0058; A61K 51/1027; A61K 51/1093; A61K 2039/505; A61P 35/00; G01N 2333/70532; G01N 2800/52; G01N 33/57407
See application file for complete search history.

(56) References Cited

U.S. PATENT DOCUMENTS

| | | | |
|---|---|---|---|
| 8,802,091 | B2 | 8/2014 | Johnson et al. |
| 9,371,395 | B2 | 6/2016 | Takahashi et al. |
| 2010/0203035 | A1 | 8/2010 | Kwon et al. |
| 2013/0149236 | A1 | 6/2013 | Johnson et al. |
| 2013/0295118 | A1 | 11/2013 | Jiang et al. |
| 2017/0073416 | A1 | 3/2017 | Couto et al. |
| 2017/0240637 | A1 | 8/2017 | Cheung et al. |
| 2017/0355769 | A1 | 12/2017 | Benatuil et al. |
| 2017/0362338 | A1 | 12/2017 | Davidson et al. |
| 2018/0371053 | A1 | 12/2018 | Dotti et al. |

FOREIGN PATENT DOCUMENTS

| | | |
|---|---|---|
| CN | 111944050 A | 11/2020 |
| KR | 20100014527 A | 2/2010 |
| WO | WO 2004/020574 A2 | 3/2004 |
| WO | WO 2010/111367 A1 | 9/2010 |
| WO | WO 2013/025834 A2 | 2/2013 |
| WO | WO 2017/180813 A1 | 10/2017 |
| WO | WO 2017/214335 A1 | 12/2017 |
| WO | WO 2018/129090 A1 | 7/2018 |
| WO | WO 2018/161872 A1 | 9/2018 |
| WO | WO 2018/177393 A1 | 10/2018 |

OTHER PUBLICATIONS

Nakakido et al. "Development of novel humanized VHH synthetic libraries based on physicochemical analyses." Scientific Reports 2023, 14:19533:1-13. (Year: 2023).*

Ahmed, M. et al., "Humanized Affinity-matured Monoclonal Antibody 8H9 Has Potent Antitumor Activity and Binds to FG Loop of Tumor Antigen B7-H3," *J. Biol. Chem.*, 290 (2015): 30018-30029.

Koenig, S., "Targeting B7-H3 in cancer," *Medicographia*, 36 (2014): 285-292.

Loo, D. et al., "Development of an Fc-enhanced anti-B7-H3 monoclonal antibody with potent antitumor activity," *Clin. Cancer Res.*, 18 (2012): 3834-3845.

(Continued)

*Primary Examiner* — Chun W Dahle
*Assistant Examiner* — Grace H Lunde
(74) *Attorney, Agent, or Firm* — pH IP Law

(57) ABSTRACT

Provided herein are agents, such as antibodies, antibody-drug conjugates, or chimeric antigen receptors, that target B7-H3. Methods of treating cancer are provided, comprising administering to a patient in need thereof an effective amount of an B7-H3-targeting agent. The patient may be selected for treatment if the cancer expresses an increased level of B7-H3.

17 Claims, 9 Drawing Sheets

Specification includes a Sequence Listing.

(56)           References Cited

OTHER PUBLICATIONS

Nagase-Zembutsu, A. et al., "Development of DS-5573a: A novel afucosylated mAb directed at B7-H3 with potent antitumor activity," *Cancer Sci.*, 107 (2016): 674-681.

Pardoll, D. M., "The blockade of immune checkpoints in cancer immunotherapy," *Nat. Rev. Cancer*, 12 (2012): 252-264.

PCT International Preliminary Report on Patentability issued in International Patent Application No. PCT/US2020/061050, mailed Jun. 2, 2022.

PCT International Search Report and Written Opinion issued in International Patent Application No. PCT/US2020/061050, mailed Apr. 7, 2021.

Seaman, S. et al., "Eradication of Tumors through Simultaneous Ablation of CD276/B7-H3-Positive Tumor Cells and Tumor Vasculature," *Cancer Cell*, 31 (2017): 501-515.

Sharma, P. et al., "Novel cancer immunotherapy agents with survival benefit: recent successes and next steps," *Nat. Rev. Cancer*, 11 (2011): 805-812.

Suh, W-K. et al., "The B7 family member B7-H3 preferentially down-regulates T helper type 1-mediated immune responses," *Nat. Immunol.*, 4 (2003): 899-906.

UniProtKB—A0A1C3KVP6 (A0A1C3KVP6_9APIC) "Uncharacterized protein" retrieved from URL: https://www.uniprot.org/uniprot/A0A1C3KVP6.

Wang, X. et al., "Blockade of both B7-H4 and CTLA-4 co-signaling pathways enhances mouse islet allograft survival," *Islets*, 4 (2012): 284-295.

Yan, R. et al., "A novel monoclonal antibody against mouse B7-H3 developed in rats," *Hybridoma*, 31 (2012): 267-271.

Zang, X. et al., "B7-H3 and B7x are highly expressed in human prostate cancer and associated with disease spread and poor outcome," *Proc. Natl. Acad. Sci. U.S.A.*, 104 (2007): 19458-19463.

Zang. X. et al., "B7x: a widely expressed B7 family member that inhibits T cell activation," *Proc. Natl. Acad. Sci. U.S.A.*, 100 (2003): 10388-10392.

Office Action issued in Chinese Patent Application No. 202080092077. X, dated May 31, 2025 (with English translation).

Conwell, J. V. et al., "Rapid antibody levels to Pseudomonas aeruginosa flagellin protein by targeted dendritic cell immunization," *Abstracts of the General Meeting of the Society for Microbiology*, (2002): abstract only.

Extended European Search Report issued in European Patent Application No. 20889500.3, Dec. 7, 2023.

Office Action issued in Chinese Patent Application No. 202080092077. X, dated Mar. 11, 2026.

Office Action issued in Korean Patent Application No. 10-2022-7020683, dated Mar. 25, 2026.

* cited by examiner

FIGS. 6A-D

ANTI-B7-H3 MONOCLONAL ANTIBODY AND METHODS OF USE THEREOF

REFERENCE TO RELATED APPLICATIONS

The present application is a national phase application under 35 U.S.C. § 371 of International Application No. PCT/US2020/061050, filed Nov. 18, 2020, which claims the priority benefit of U.S. provisional application No. 62/936,783, filed Nov. 18, 2019, the entire contents of each of which are incorporated herein by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Nov. 4, 2020, is named UTFCP1481WO_ST25.txt and is 6.9 kilobytes in size.

BACKGROUND

1. Field

The present invention relates generally to the fields of medicine, immunology, and cancer biology. More particularly, it concerns antibodies that target B7-H3 and methods of their use.

2. Description of Related Art

Harnessing the host immune system through attenuation of endogenous immune checkpoints on effector T cells has led to dramatic and sustained tumor response in selected solid tumor patients (Sharma et al., 2011). Antibodies that block co-inhibitory T-cell signals, such as those targeted against CTLA-4, PD-1, and PD-L1, have demonstrated objective response rates in 10-30% of patients with a variety of solid cancers that would otherwise be fatal, including metastatic melanoma, RCC, NSCLC, and ovarian cancer, and many promising immune checkpoint therapies (ICT) as monotherapy and combination trials are underway. However, toxic side effects are substantial, while many patients are resistance to ICT, and thus, novel means for blocking the immune checkpoint for therapeutic purposes are needed.

SUMMARY

In one embodiment, provided herein are monoclonal antibodies or antibody fragments, wherein the antibodies or antibody fragments comprise a heavy chain variable region (VH) comprising VHCDR1, VHCDR2, and VHCDR3 amino acid sequences from the MIL33B antibody; and a light chain variable region (VL) comprising VLCDR1, VLCDR2, and VLCDR3 amino acid sequences from the MIL33B antibody.

In some aspects, the antibodies or antibody fragments comprise a heavy chain variable region (VH) comprising VHCDR1, VHCDR2, and VHCDR3 amino acid sequences derived from SEQ ID NO: 7; and a light chain variable region (VL) comprising VLCDR1, VLCDR2, and VLCDR3 amino acid sequences derived from SEQ ID NO: 8. In some aspects, the antibodies or antibody fragments are capable of binding to B7-H3.

In some aspects, the antibodies or antibody fragments comprise a heavy chain variable region (VH) comprising a VHCDR1 amino acid sequence of SEQ ID NO: 1, a VHCDR2 amino acid sequence of SEQ ID NO: 2, and a VHCDR3 amino acid sequence of SEQ ID NO: 3; and a light chain variable region (VL) comprising a VLCDR1 amino acid sequence of SEQ ID NO: 4, a VLCDR2 amino acid sequence of SEQ ID NO: 5, and a VLCDR3 amino acid sequence of SEQ ID NO: 6.

In some aspects, the antibodies or antibody fragments comprise a heavy chain variable region (VH) comprising a VHCDR1 amino acid sequence of SEQ ID NO: 11, a VHCDR2 amino acid sequence of SEQ ID NO: 12, and a VHCDR3 amino acid sequence of SEQ ID NO: 13; and a light chain variable region (VL) comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In some aspects, the antibodies or antibody fragments comprise a heavy chain variable region (VH) comprising a VHCDR1 amino acid sequence of SEQ ID NO: 17, a VHCDR2 amino acid sequence of SEQ ID NO: 18, and a VHCDR3 amino acid sequence of SEQ ID NO: 19; and a light chain variable region (VL) comprising a VLCDR1 amino acid sequence of SEQ ID NO: 20, a VLCDR2 amino acid sequence of SEQ ID NO: 21, and a VLCDR3 amino acid sequence of SEQ ID NO: 6.

In some aspects, the antibodies or antibody fragments comprise a heavy chain variable region (VH) comprising a VHCDR1 amino acid sequence of SEQ ID NO: 17, a VHCDR2 amino acid sequence of SEQ ID NO: 18, and a VHCDR3 amino acid sequence of SEQ ID NO: 19; and a light chain variable region (VL) comprising a VLCDR1 amino acid sequence of SEQ ID NO: 4, a VLCDR2 amino acid sequence of SEQ ID NO: 5, and a VLCDR3 amino acid sequence of SEQ ID NO: 6.

In some aspects, the antibodies or antibody fragments comprise a heavy chain variable sequence having at least 70%, 80%, or 90% identity to SEQ ID NO: 7 and a light chain variable sequence having at least 70%, 80%, or 90% identity to SEQ ID NO: 8. In some aspects, the antibodies or antibody fragments comprise a heavy chain variable sequence having at least 95% identity to SEQ ID NO: 7 and a light chain variable sequence having at least 95% identity to SEQ ID NO: 8. In some aspects, the antibodies or antibody fragments comprise a heavy chain variable sequence having a sequence according to SEQ ID NO: 7 and a light chain variable sequence having a sequence according to SEQ ID NO: 8.

In some aspects, the antibodies or antibody fragments are humanized. In some aspects, the antibody fragments are monovalent scFv (single chain fragment variable) antibodies, divalent scFv's, Fab fragments, F(ab')$_2$ fragments, F(ab')$_3$ fragments, Fv fragments, or single chain antibodies. In some aspects, the antibodies are chimeric antibodies, bispecific antibodies, or BiTE's. In some aspects, the antibodies are IgG antibodies or recombinant IgG antibodies or antibody fragments.

In one embodiment, provided herein are monoclonal antibodies or antibody fragments that compete for binding to the same epitope as the monoclonal antibody or an antibody fragment according to any one the present embodiments.

In one embodiment, provided herein are monoclonal antibodies or antibody fragments that bind to an epitope on B7-H3 recognized by an antibody of any one the present embodiments.

In some aspects, the antibodies or antibody fragments are conjugated or fused to an imaging agent, a cytotoxic agent, a metal, or a radioactive moiety. In some aspects, the imaging agent is a fluorophore. In some aspects, the radio-active moiety is Zr-89, Cu-64, F-18, Y-90, Lu-177, At-211, Ac-225, or Pb-212.

In some aspects, the antibodies or antibody fragments are immune conjugates. In some aspects, the antibodies or antibody fragments are conjugated to flagellin or a flagellin derivative.

In some aspects, the antibodies or antibody fragments are antibody-drug conjugates.

In one embodiment, provided herein are isolated nucleic acids encoding the antibody heavy and/or light chain vari-able regions of the antibody molecules of any of the present embodiments. In some aspects, the nucleic acids comprise a nucleotide sequence that is at least 85% identical to SEQ ID NO: 9. In some aspects, the nucleic acids comprise a nucleotide sequence that is at least 85% identical to SEQ ID NO: 10.

In one embodiment, provided herein are expression vec-tors comprising the nucleic acids of any one of the present embodiments.

In one embodiment, provided herein are hybridomas or engineered cells comprising the nucleic acids encoding the antibodies or antibody fragments of any one of the present embodiments.

In one embodiment, provided herein are methods of making the monoclonal antibodies or antibody fragments of any one of the present embodiments, the methods compris-ing culturing the hybridomas or engineered cells of the present embodiments under conditions that allow expression of the antibodies and optionally isolating the antibodies from the culture.

In one embodiment, provided herein are pharmaceutical formulations comprising one or more antibody or antibody fragment of any one of the present embodiments.

In one embodiment, provided herein are methods of treating a patient having a cancer, the methods comprising administering an effective amount of the antibodies or antibody fragments of any one of the present embodiments. In some aspects, the cancer has been determined to express an elevated level of B7-H3 relative to a healthy tissue. In some aspects, the cancer is a renal cancer, a pancreatic cancer, a colorectal cancer, a non-small cell lung cancer, an ovarian cancer, a bladder cancer, a melanoma, a prostate cancer, a breast cancer, a glioma, a lymphoma, or a neu-roectodermal cancer. In some aspects, the methods further comprise administering at least a second anti-cancer therapy. In certain aspects, the second anti-cancer therapy is a chemotherapy, targeted anti-cancer therapy, immunotherapy, radiotherapy, radioimmunotherapy, phototherapy, gene therapy, surgery, hormonal therapy, epigenetic modulation, anti-angiogenic therapy or cytokine therapy. In some aspects, the patient has previously failed to respond to an immune checkpoint inhibitor. In some aspects, the patient has relapsed.

In one embodiment, provided herein are chimeric antigen receptor (CAR) proteins comprising an antigen binding domain comprising a heavy chain variable region (VH) comprising VHCDR1, VHCDR2, and VHCDR3 amino acid sequences from the MIL33B antibody; and a light chain variable region (VL) comprising VLCDR1, VLCDR2, and VLCDR3 amino acid sequences from the MIL33B antibody.

In some aspects, the antigen binding domain comprises a heavy chain variable region (VH) comprising VHCDR1, VHCDR2, and VHCDR3 amino acid sequences derived from SEQ ID NO: 7; and a light chain variable region (VL) comprising VLCDR1, VLCDR2, and VLCDR3 amino acid sequences derived from SEQ ID NO: 8.

In some aspects, the antigen binding domain comprises heavy and light chain CDR sequences as follows: a heavy chain variable region (VH) comprising a VHCDR1 amino acid sequence of SEQ ID NO: 1, a VHCDR2 amino acid sequence of SEQ ID NO: 2, and a VHCDR3 amino acid sequence of SEQ ID NO: 3; and a light chain variable region (VL) comprising a VLCDR1 amino acid sequence of SEQ ID NO: 4, a VLCDR2 amino acid sequence of SEQ ID NO: 5, and a VLCDR3 amino acid sequence of SEQ ID NO: 6.

In some aspects, the antigen binding domain comprises heavy and light chain CDR sequences as follows: a heavy chain variable region (VH) comprising a VHCDR1 amino acid sequence of SEQ ID NO: 11, a VHCDR2 amino acid sequence of SEQ ID NO: 12, and a VHCDR3 amino acid sequence of SEQ ID NO: 13; and a light chain variable region (VL) comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In some aspects, the antigen binding domain comprises heavy and light chain CDR sequences as follows: a heavy chain variable region (VH) comprising a VHCDR1 amino acid sequence of SEQ ID NO: 17, a VHCDR2 amino acid sequence of SEQ ID NO: 18, and a VHCDR3 amino acid sequence of SEQ ID NO: 19; and a light chain variable region (VL) comprising a VLCDR1 amino acid sequence of SEQ ID NO: 20, a VLCDR2 amino acid sequence of SEQ ID NO: 21, and a VLCDR3 amino acid sequence of SEQ ID NO: 6.

In some aspects, the antigen binding domain comprises heavy and light chain CDR sequences as follows: a heavy chain variable region (VH) comprising a VHCDR1 amino acid sequence of SEQ ID NO: 17, a VHCDR2 amino acid sequence of SEQ ID NO: 18, and a VHCDR3 amino acid sequence of SEQ ID NO: 19; and a light chain variable region (VL) comprising a VLCDR1 amino acid sequence of SEQ ID NO: 4, a VLCDR2 amino acid sequence of SEQ ID NO: 5, and a VLCDR3 amino acid sequence of SEQ ID NO: 6.

In some aspects, the antigen binding domains are capable of binding to B7-H3. In some aspects, the antigen binding domains are humanized antigen-binding domains.

In some aspects, the antigen binding domains comprise a heavy chain variable sequence having at least 70%, 80%, or 90% identity to SEQ ID NO: 7 and a light chain variable sequence having at least 70%, 80%, or 90% identity to SEQ ID NO: 8. In some aspects, the antigen binding domains comprise a heavy chain variable sequence having at least 95% identity to SEQ ID NO: 7 and a light chain variable sequence having at least 95% identity to SEQ ID NO: 8. In some aspects, the antigen binding domains comprise a heavy chain variable sequence having a sequence according to SEQ ID NO: 7 and a light chain variable sequence having a sequence according to SEQ ID NO: 8.

In some aspects, the CAR proteins further comprise a hinge domain, a transmembrane domain, and an intracellular signaling domain. In some aspects, the hinge domain is a CD8a hinge domain or an IgG4 hinge domain. In some aspects, the transmembrane domain is a CD8a transmem-brane domain or a CD28 transmembrane domain. In some aspects, the intracellular signaling domain comprises a CD3ζ intracellular signaling domain.

In one embodiment, provided herein are nucleic acid molecules encoding a CAR of any one of the present embodiments. In some aspects, the sequence encoding the CAR is operatively linked to expression control sequences. In some aspects, the nucleic acids are further defined as expression vectors.

In one embodiment, provided herein are engineered cells comprising a nucleic acid molecule encoding a chimeric antigen receptor (CAR) of any one of the present embodiments. In some aspects, the cell is a T cell. In some aspects, the cell is an NK cell. In some aspects, the nucleic acid is integrated into the genome of the cell. In some aspects, the cell is a human cell.

In one embodiment, provided herein are pharmaceutical compositions comprising a population of cells in accordance with any one of the present embodiments in a pharmaceutically acceptable carrier.

In one embodiment, provided herein are methods of treating cancer in a human patient in need thereof comprising administering to the patient an anti-tumor effective amount of a cell therapy comprising one or more cells in accordance with any one of the present embodiments. In some aspects, the cells are allogeneic cells. In some aspects, the cells are autologous cells. In some aspects, the cells are HLA matched to the subject. In some aspects, the cancer has been determined to express an elevated level of B7-H3 relative to a healthy tissue. In some aspects, the cancer is a renal cancer, a pancreatic cancer, a colorectal cancer, a non-small cell lung cancer, an ovarian cancer, a bladder cancer, a melanoma, a prostate cancer, a breast cancer, a glioma, a lymphoma, or a neuroectodermal cancer.

In some aspects, the methods further comprise administering at least a second anti-cancer therapy. In some aspects, the second anti-cancer therapy is a chemotherapy, molecular targeted therapy, immunotherapy, radiotherapy, radioimmunotherapy, phototherapy, gene therapy, surgery, hormonal therapy, epigenetic modulation, anti-angiogenic therapy or cytokine therapy. In some aspects, the patient has previously failed to respond to an immune checkpoint inhibitor. In some aspects, the patient has relapsed.

In one embodiment, provided herein are methods of diagnosing a patient as having a cancer that expresses B7-H3, the methods comprising contacting a cancer tissue obtained from the patient with an antibody or antibody fragment of any one of the present embodiments and detecting the binding of the antibody or antibody fragment to the tissue, wherein if the antibody or antibody fragment binds to the tissue, then the patient is diagnosed as having a cancer that expresses B7-H3. In some aspects, detecting comprises performing ELISA, immunoblotting, immunohistochemistry, multispectral fluorescence cytometric imaging, FACS, mass cytometry (CyTOF), imaging mass cytometry (IMC), optical imaging, PET imaging, SPECT imaging, or MRI. In some aspects, the methods further comprise administering to the patient diagnosed as having a cancer that expresses B7-H3 an effective amount of antibody or antibody fragment or a cell therapy comprising one or more cells in accordance with any one of the present embodiments.

In one embodiment, provided herein are methods of selecting a patient having a cancer for treatment with an anti-B7-H3 antibody, the method comprising (a) determining whether the cancer expresses B7-H3, and (b) selecting the patient for treatment if B7-H3 is expressed by the cancer. In some aspects, step (a) comprises (i) obtaining or having obtained a biological sample from the patient; and (ii) performing or having performed an assay on the biological sample to determine whether B7-H3 is expressed in the cancer. In some aspects, the methods further comprise administering to the selected patient an effective amount of antibody or antibody fragment or a cell therapy comprising one or more cells in accordance with any one of the present embodiments.

In some aspects, whether B7-H3 is expressed in the cancer is determined by detecting an B7-H3 protein in the sample. In some aspects, the protein is detected by mass cytometry, imaging mass cytometry, Western blot, FACS, immunohistochemistry, ELISA, RIA, optical imaging, PET imaging, SPECT imaging, or MRI. In some aspects, the protein is detected by contacting a sample of the cancer with an antibody of any one of the present embodiments.

In one embodiment, provided herein are methods for detecting the presence of B7-H3 on the surface of a cell, in a tissue, in an organ, or an in a biological sample, the method comprising (a) contacting the cell, tissue, organ, or biological sample with an antibody of any one of the present embodiments; and (b) detecting the presence of the antibody associated with the cell, tissue, organ, or sample. In some aspects, the contacting and detecting are in vitro. In some aspects, the contacting is in vivo and the detecting is in vitro. In certain aspects, the imaging agent is a fluorophore or chromophore. In some aspects, the contacting and detecting are in vivo. In certain aspects, the imaging agent is a radionuclide. In certain aspects, the detection is by PET, SPECT, MRI, or hyperpolarized MRI. In certain aspects, the detection is by hyperpolarized MRI, wherein the detectable label is a Si-29 nanoparticle.

In one embodiment, provided herein are methods of performing fluorescence-guided surgery, the method comprising (a) administering a composition comprising an antibody conjugate of the present embodiments to a patient under conditions and for a time sufficient for the antibody to accumulate at a given surgical site; (b) illuminating the surgical site with an excitation light to cause an emission from the fluorescent moiety; and (c) performing surgical resection of the areas that fluoresce upon excitation by the excitation light.

In one embodiment, provided herein are antibody molecules or pharmaceutical compositions of any one of the present embodiments, for use in treating a cancer in a subject.

In one embodiment, provided herein are uses of antibody molecules or pharmaceutical compositions of any one of the present embodiments, in the manufacture of a medicament for treating a cancer in a subject.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A shows high signal from human HeLa and HCT116 cells expressing native 4Ig-B7-H3. Note the low background fluorescence from cell autofluorescence or from labeled IgG2a. Furthermore, cell fluorescence is reduced to background when Alexa594-labeled MIL33B is added in the presence of molar excess unlabeled MIL33B, demonstrating specificity. FIG. 4B shows murine 4T1 cells expressing moderate native 2Ig-B7-H3 and engineered to express human 4Ig-B7-H3 or empty vector control. FIG. 4C shows murine Pan02 cells expressing 2Ig-B7-H3.

FIG. 6A illustrates the 1B-RE₅-IκBα-Fluc reporter. FIG. 6B shows the initial loss of light production from TNF-α-induced (time=0) loss of the IκBα-Fluc reporter followed by an increase in light production from the κB response element (RE₅)-induced re-synthesis of IκBα-Fluc. MIL33B alone does not activate NF-κB signaling. FIG. 6C shows the initial loss of light production, followed by increase in light production from the κB response element (RE₅) driving re-synthesis of IκBα-Fluc following treatment with flagellin and flagellin-conjugated MIL33B. FIG. 6D shows the levels of IκBα-Fluc-mediated photon flux elicited by flagellin-conjugated MIL33B and various concentrations of flagellin alone at 4 hours post-stimulation.

There is signal equivalency between 1.8 nM flagellin and 18.2 nM MIL33B-flagellin conjugate.

Figure 7:
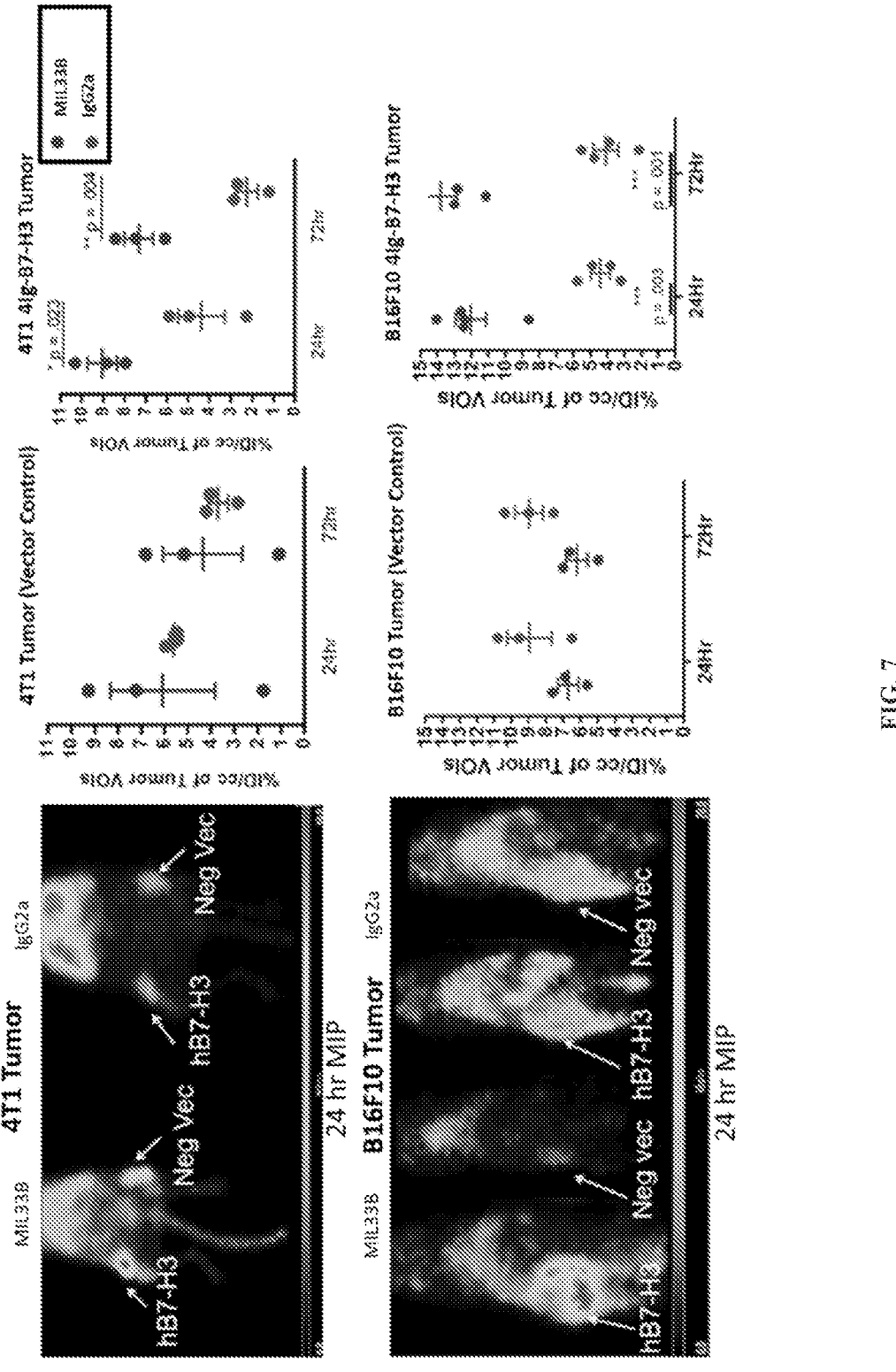

FIG. 7. Detection in vivo of 4T1 murine mammary and B16F10 murine melanoma tumors expressing human 4Ig-B7-H3 or vector control by PET imaging using MIL33B conjugated to DFO and radiolabeled with $^{89}$Zr compared to isotype control IgG2a conjugated to DFO and radiolabeled with $^{89}$Zr. Coronal PET images as maximum intensity projections (MIP) are shown (left panels) as well as volumetric analysis (% ID/cc) at 24 hrs and 72 hrs post-injection of the radiolabeled MIL33B or isotype control antibodies (mid and right panels). In the mid and right panels, for each pair of columns, the left column represents MIL33B and the right column represents IgG2a.

Figure 8:
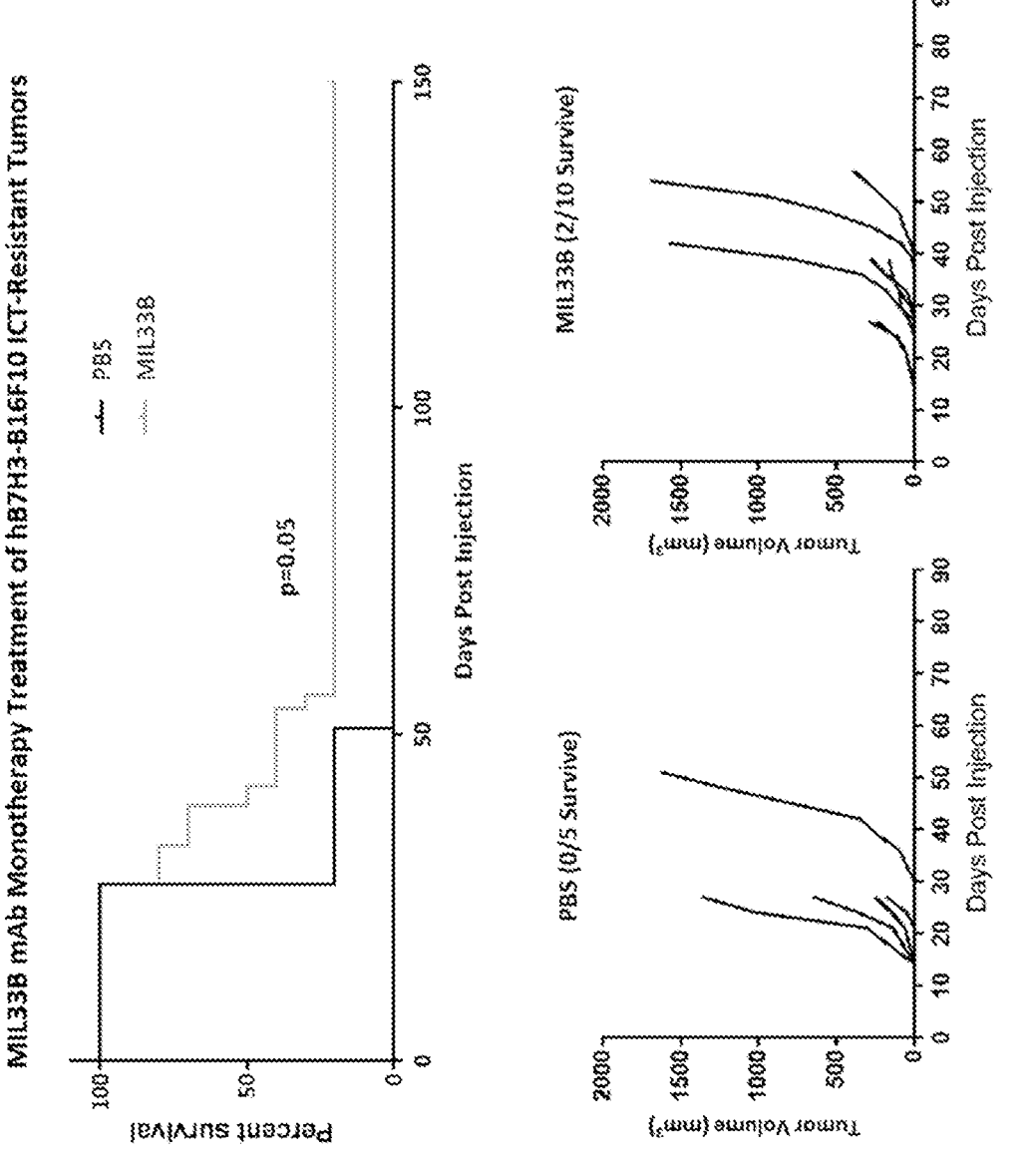

FIG. 8. Survival curves (top) and tumor growth curves (bottom) of mice harboring murine B16F10 tumors expressing 4Ig-B7-H3 treated with MIL33B monotherapy or untreated control (PBS vehicle).

DETAILED DESCRIPTION

B7-H3 is a co-inhibitory ligand expressed on the surface of many tumor cells as well as in the tumor microvasculature (Suh et al., 2003; Zang et al., 2007; Wang et al., 2012). It is thought to actively inhibit the effector functions of cytotoxic T lymphocytes (CTLs) or induce the generation of regulatory T cells, all of which down-regulate immune responses (Pardon, 2012). Although CTLA-4 and B7-H3 are both members of the extended CD28/B7 family, CTLA-4 and B7-H3 have non-overlapping functions, and studies conducted in animal models suggest that the two pathways play distinct roles in immune regulation (Zang et al., 2007; Wang et al., 2012).

B7-H3 protein is expressed on most tumor cell types as well as tumor-associated vasculature (Seaman et al., 2017). For example, B7-H3 is overexpressed on renal, pancreatic, colorectal, non-small cell lung, ovarian, bladder, melanoma, and neuroectodermal cancers (Loo et al., 2012), as well as prostate cancer cells (Zang et al., 2007; Koenig, 2014), pointing to the broad applicability of targeting B7-H3 for therapy and imaging. For example, in prostatectomy specimens from 803 patients with localized disease, the vast majority (93%) of the prostate tumors expressed B7-H3 (Zang et al., 2007). Furthermore, high level expression of B7-H3 (and/or B7-H4, another co-inhibitory ligand) was associated with higher risk of clinical failure (metastases) and of death within 7 years, implicating these molecules as inhibitory immune checkpoints that act to suppress anti-tumor immune responses (Zang et al., 2007; Zang et al., 2003). In addition, renal, melanoma, glioblastoma, thyroid and pancreatic cancers show up to 99% positive staining for B7-H3 by IHC (Koenig, 2014). Most significantly, there is limited B7-H3 protein in normal human tissues (Koenig, 2014; Zang et al., 2003). Because B7-H3 is highly expressed on the surface of cancer cells as well as cancer vasculature, but not normal tissues, B7-H3 provides an excellent target for anti-cancer immuno-therapy, positron emission tomography (PET) and immuno-PET imaging, and bifunctional-conjugate drug therapy.

Known anti-B7-H3 antibodies demonstrate modest nano-molar affinity for only human or only mouse B7-H3 [PMID: 22894780, PMID: 26487718, PMID: 28399408, PMID: 22615450]. These antibodies have been developed in normal mice that have murine 2Ig-B7-H3, which demonstrates high homology and domain identity to human 4Ig-B7-H3 and human 2Ig-B7-H3. Thus, thymic-induced tolerance to self-antigens may limit the repertoire of epitopes discoverable in normal mice strains, such as the common C57B16 strain. Further, B7-H3 has significant homology to other paralogues of the B7 family, further restricting the accessibility of high affinity epitopes discoverable in either normal or in B7-H3-knockout mice.

While human-only affinity is clearly sufficient for clinical translation and desired therapeutic applications, it renders pre-clinical murine models difficult or impossible to perform because a human-only antibody cannot recognize murine epitopes. In today's era of combination therapies with immune checkpoint inhibitors, this becomes particularly problematic and requires the use of murine surrogate active antibodies. On the other hand, antibodies that recognize only murine epitopes will enable pre-clinical analysis in appropriate murine models, but preclude translation to humans. The ideal monoclonal antibody would display high affinity to epitopes common to both human and murine targets, in this case, B7-H3.

As such, provided herein is a monoclonal antibody, MIL33B, with high dual-species affinity for human 4Ig-B7-H3 (picomolar) and mouse 2Ig-B7-H3 (nanomolar). MIL33B was developed from an immunized New Zealand Black/White (NZBWF1/J) mouse, a strain with broken tolerance. MIL33B antibody has higher affinity than any published or commercialized antibody to human 4Ig-B7-H3. For moderate abundant targets on the tumor and human immune system, affinity is crucial for maximizing immune-reactive processes, such as antibody-dependent cellular cytotoxicity (ADCC), antibody drug conjugate (ADC) therapy, radiotherapy and imaging, and will always be beneficial for functional inhibition of linked biology, particularly when local concentrations of competing ligands might be high. All of the published Kd values for commercialized antibodies, e.g., ch8H9 mAbs (Ahmed et al., 2015) and Macrogenics (Loo et al., 2012), are >5 nM (or 5,000 pM), which represents a >25-fold affinity advantage for MIL33B. The MIL33B antibody can be used at least in immuno-therapy, combination immune checkpoint therapy, antibody-conjugates, antibody-based radio-therapeutics, antibody-based PET/SPECT imaging agents, antibody-based in vitro diagnostics.

I. Definitions

"Nucleic acid," "nucleic acid sequence," "oligonucle-otide," "polynucleotide" or other grammatical equivalents as used herein means at least two nucleotides, either deoxyribonucleotides or ribonucleotides, or analogs thereof, covalently linked together. Polynucleotides are polymers of any length, including, e.g., 20, 50, 100, 200, 300, 500, 1000, 2000, 3000, 5000, 7000, 10,000, etc. A polynucleotide described herein generally contains phosphodiester bonds, although in some cases, nucleic acid analogs are included that may have at least one different linkage, e.g., phosphoramidate, phosphorothioate, phosphorodithioate, or O-methylphophoroamidite linkages, and peptide nucleic acid backbones and linkages. Mixtures of naturally occurring polynucleotides and analogs can be made; alternatively, mixtures of different polynucleotide analogs, and mixtures of naturally occurring polynucleotides and analogs may be made. The following are non-limiting examples of polynucleotides: a gene or gene fragment, exons, introns, messenger RNA (mRNA), transfer RNA, ribosomal RNA, ribozymes, cDNA, cRNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, the term polynucleotide encompasses both the double-stranded form and each of two complementary single-stranded forms known or predicted to make up the double-stranded form. A polynucleotide is composed of a specific sequence of four nucleotide bases: adenine (A), cytosine (C), guanine (G), thymine (T), and uracil (U) for thymine when the polynucleotide is RNA. Thus, the term "polynucleotide sequence" is the alphabetical representation of a polynucleotide molecule. Unless otherwise indicated, a particular polynucleotide sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The terms "peptide," "polypeptide" and "protein" used herein refer to polymers of amino acid residues. These terms also apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers. In the present case, the term "polypeptide" encompasses an antibody or a fragment thereof.

Other terms used in the fields of recombinant nucleic acid technology, microbiology, immunology, antibody engineering, and molecular and cell biology as used herein will be generally understood by one of ordinary skill in the applicable arts.

II. Antibodies and Modifications of Antibodies

Provided herein are monoclonal antibodies having clone-paired complementarity-determining regions (CDRs) from the heavy and light chains as illustrated in Tables 1-3. Such antibodies may be produced using methods described herein.

The monoclonal antibodies of the present invention have several applications, including the production of diagnostic kits for use in detecting B7-H3, as well as for treating diseases associated with increased levels of B7-H3. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv, Fd, Fd', single chain antibody (ScFv), diabody, linear antibody), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular instances, the antibody is purified: (1) to greater than 95% by weight of antibody as determined by the Lowry method, and most particularly more than 99% by weight; or (2) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, an isolated antibody will be prepared by at least one purification step.

The basic four-chain antibody unit is a heterotetrameric glycoprotein composed of two identical light (L) chains and two identical heavy (H) chains. The term "heavy chain" as used herein refers to the larger immunoglobulin subunit which associates, through its amino terminal region, with the immunoglobulin light chain. The heavy chain comprises a variable region ($V_H$) and a constant region ($C_H$). The constant region further comprises the $C_H1$, hinge, $C_H2$, and $C_H3$ domains. In the case of IgE, IgM, and IgY, the heavy chain comprises a $C_H4$ domain but does not have a hinge domain. Those skilled in the art will appreciate that heavy chains are classified as gamma, mu, alpha, delta, or epsilon ($\gamma$, $\mu$, $\alpha$, $\delta$, $\varepsilon$), with some subclasses among them (e.g., $\gamma1$-$\gamma4$, $\alpha1$-$\alpha2$). It is the nature of this chain that determines the "class" of the antibody as IgG, IgM, IgA IgD, or IgE, respectively. The immunoglobulin subclasses (isotypes), e.g., IgG1, IgG2, IgG3, IgG4, IgA1, etc. are well characterized and are known to confer functional specialization.

The term "light chain" as used herein refers to the smaller immunoglobulin subunit which associates with the amino terminal region of a heavy chain. As with a heavy chain, a light chain comprises a variable region ($V_L$) and a constant region ($C_L$). Light chains are classified as either kappa or lambda ($\kappa$, $\lambda$) based on the amino acid sequences of their constant domains ($C_L$). A pair of these can associate with a pair of any of the various heavy chains to form an immunoglobulin molecule. Also encompassed in the meaning of light chain are light chains with a lambda variable region (V-lambda) linked to a kappa constant region (C-kappa) or a kappa variable region (V-kappa) linked to a lambda constant region (C-lambda).

An IgM antibody, for example, consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes.

Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

A "variable region" of an antibody refers to the variable region of the antibody light chain or the variable region of the antibody heavy chain, either alone or in combination. The term "variable" refers to the fact that certain segments of the variable regions differ extensively in sequence among antibodies. The variable regions of both the light ($V_L$) and heavy ($V_H$) chain portions mediate antigen binding and define the specificity of a particular antibody for its particular antigen. However, the variability is not evenly distributed across the entirety of the variable regions. Instead, the variable regions consist of relatively invariant stretches called framework regions (FRs) separated by shorter regions of extreme variability called complementarity determining regions (CDRs) or hypervariable regions. The variable regions of native heavy and light chains each comprise four FRs, largely adopting a beta-sheet configuration, connected by three CDRs, which form loops connecting, and in some cases forming part of, the beta-sheet structure. The CDRs complement an antigen's shape and determine the antibody's affinity and specificity for the antigen. There are six CDRs in both $V_L$ and $V_H$. The CDRs in each chain are held together in close proximity by the FRs and, with the CDRs from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)). As used herein, a CDR may refer to CDRs defined by any of these numbering approaches or by a combination of approaches or by other desirable approaches. In addition, a new definition of highly conserved core, boundary and hyper-variable regions can be used.

A "constant region" of an antibody refers to the constant region of the antibody light chain or the constant region of the antibody heavy chain, either alone or in combination. The constant regions of the light chain ($C_L$) and the heavy chain ($C_H1$, $C_H2$ or $C_H3$, or $C_H4$ in the case of IgM and IgE) confer important biological properties such as secretion, transplacental mobility, Fc receptor binding, complement binding, and the like. By convention the numbering of the constant region domains increases as they become more distal from the antigen binding site or amino-terminus of the antibody. The constant regions are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The antibody may be an antibody fragment. "Antibody fragments" comprise only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_{H1}$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the $C_H1$ domain; (v) the Fv fragment having the $V_L$ and $V_H$ domains of a single antibody; (vi) the dAb fragment which consists of a $V_H$ domain; (vii) isolated CDR regions; (viii) F(ab')2 fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain ($V_H$) connected to a light chain variable domain ($V_L$) in the same polypeptide chain; (xi) "linear antibodies" comprising a pair of tandem Fd segments ($V_H$—$C_H1$-$V_H$-$C_H1$) which, together with complementary light chain polypeptides, form a pair of antigen binding regions.

The antibody may be a chimeric antibody. "Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. For example, a chimeric antibody may be an antibody comprising antigen binding sequences from a non-human donor grafted to a heterologous non-human, human, or humanized sequence (e.g., framework and/or constant domain sequences). Typically, in these chimeric antibodies, the variable region of both light and heavy chains mimics the variable regions of antibodies derived from one species of mammals, while the constant portions are homologous to the sequences in antibodies derived from another. For example, methods have been developed to replace light and heavy chain constant domains of a monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557, incorporated herein by reference). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

A. Monoclonal Antibodies

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256: 495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The monoclonal antibodies may also be isolated from phage antibody libraries using the techniques described in Clackson et al., Nature, 352: 624-628 (1991) and Marks et al., J. Mol. Biol., 222:581-597 (1991), for example.

Methods for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196, 265; 4,275,149; 4,277,437; 4,366,241; 4,469,797; 4,472, 509; 4,606,855; 4,703,003; 4,742,159; 4,767,720; 4,816, 567; 4,867,973; 4,938,948; 4,946,778; 5,021,236; 5,164, 296; 5,196,066; 5,223,409; 5,403,484; 5,420,253; 5,565, 332; 5,571,698; 5,627,052; 5,656,434; 5,770,376; 5,789, 208; 5,821,337; 5,844,091; 5,858,657; 5,861,155; 5,871, 907; 5,969,108; 6,054,297; 6,165,464; 6,365,157; 6,406, 867; 6,709,659; 6,709,873; 6,753,407; 6,814,965; 6,849, 259; 6,861,572; 6,875,434; and 6,891,024, each incorporated herein by reference.

B. Single Chain Antibodies

A single chain variable fragment (scFv) is a fusion of the variable regions of the heavy and light chains of immunoglobulins, linked together with a short linker. This chimeric molecule retains the specificity of the original immuno-globulin, despite removal of the constant regions and the introduction of a linker peptide. This modification usually leaves the specificity unaltered. scFv can be created directly from subcloned heavy and light chains derived from a hybridoma or B cell. Single chain variable fragments lack the constant Fc region found in complete antibody mol-ecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. For example, the linker may have a proline residue two residues after the $V_H$ C terminus and an abundance of arginines and prolines at other positions.

A single-chain antibody may also be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contem-plated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable sta-bility in blood will be employed. Numerous types of disul-fide-bond containing linkers are known that can be success-fully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

For example, SMPT is a bifunctional cross-linker con-taining a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site. The SMPT cross-linking reagent, as with many other known cross-linking reagents, lends the ability to cross-link func-tional groups such as the SH of cysteine or primary amines (e.g., the epsilon amino group of lysine). Another possible type of cross-linker includes the hetero-bifunctional photo-reactive phenylazides containing a cleavable disulfide bond such as sulfosuccinimidyl-2-(p-azido salicylamido)ethyl-1, 3'-dithiopropionate. The N-hydroxy-succinimidyl group reacts with primary amino groups and the phenylazide (upon photolysis) reacts non-selectively with any amino acid resi-due.

In addition to hindered cross-linkers, non-hindered linkers also can be employed in accordance herewith. Other useful cross-linkers, not considered to contain or generate a pro-tected disulfide, include SATA, SPDP and 2-iminothiolane. The use of such cross-linkers is well understood in the art. Flexible linkers may also be used.

U.S. Pat. No. 4,680,338, describes bifunctional linkers useful for producing conjugates of ligands with amine-containing polymers and/or proteins, especially for forming antibody conjugates with chelators, drugs, enzymes, detect-able labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion pro-teins, e.g., single chain antibodies. The linker is up to about 50 amino acids in length, contains at least one occurrence of a charged amino acid (preferably arginine or lysine) fol-lowed by a proline, and is characterized by greater stability and reduced aggregation. U.S. Pat. No. 5,880,270 discloses aminooxy-containing linkers useful in a variety of immu-nodiagnostic and separative techniques.

C. Bispecific and Multispecific Antibodies

Antibodies may be bispecific or multispecific. "Bispecific antibodies" are antibodies that have binding specificities for at least two different epitopes. Exemplary bispecific anti-bodies may bind to two different epitopes of a single antigen. Other such antibodies may combine a first antigen binding site with a binding site for a second antigen. Alternatively, an antigen-specific arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibod-ies may also be used to localize cytotoxic agents to infected cells. These antibodies possess an antigen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')₂ bispecific antibodies). Taki et al. (2015) describes a bispecific anti-B7-H3/anti-CD3 antibody.

Methods for making bispecific antibodies are known in the art. Traditional production of full-length bispecific anti-bodies is based on the co-expression of two immunoglobulin heavy chain-light chain pairs, where the two chains have different specificities. Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low.

According to a different approach, antibody variable regions with the desired binding specificities (antibody-antigen combining sites) are fused to immunoglobulin con-stant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

The bispecific antibodies may be composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from E. coli, which can be chemically coupled to form bispecific antibodies. Shalaby et al., J. Exp. Med., 175: 217-225 (1992) describe the production of a humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., Nat. Biotechnol. 16, 677-681 (1998)). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

A bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400). Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264; Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., Science, 358(6359):85-90, 2017). The antibodies may also involve sequences or moieties that permit dimerization or multimerization of the receptors. Such sequences include those derived from IgA, which permit formation of multimers in conjunction with the J-chain. Another multimerization domain is the Gal4 dimerization domain.

A multivalent antibody may be internalized (and/or catabolized) faster than a bivalent antibody by a cell expressing an antigen to which the antibody binds. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. Multivalent antibodies may comprise (or consist of) three to about eight, for example four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1).sub.n-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

D. BiTES

A bi-specific T-cell engagers (BITE®) is an artificial bispecific monoclonal antibody that directs a host's immune system, more specifically the T cells' cytotoxic activity, to target diseased cells. BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic activity on target cells by producing proteins like perforin and granzymes, independently of the presence of MHC I or co-stimulatory molecules. These proteins enter the target cells and initiate apoptosis. This action mimics physiological processes observed during T cell attacks against infected cells.

E. Antibody Conjugates

Antibodies of the present disclosure may be linked to at least one agent to form an antibody conjugate. The conjugate can be, for example, an antibody conjugated to another proteinatious, carbohydrate, lipid, or mixed moiety molecule(s). Such antibody conjugates include, but are not limited to, modifications that include linking the antibody to one or more polymers. For example, an antibody may be linked to one or more water-soluble polymers. Linkage to a water-soluble polymer reduces the likelihood that the antibody will precipitate in an aqueous environment, such as a physiological environment. One skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, an enzyme (e.g., that catalyzes a colorimetric or fluorometric or bioluminescent reaction), a substrate, a solid matrix, such as biotin. An antibody may comprise one, two, or more of any of these labels.

Antibody conjugates may be used to deliver cytotoxic agents to target cells. Cytotoxic agents of this type may improve antibody-mediated cytotoxicity, and include such moieties as cytokines that directly or indirectly stimulate cell death, radioisotopes, chemotherapeutic drugs (including prodrugs), bacterial toxins (e.g., *Pseudomonas* exotoxin, diphtheria toxin, etc.), plant toxins (e.g., ricin, gelonin, etc.), chemical conjugates (e.g., maytansinoid toxins, calechaemicin, etc.), radioconjugates, enzyme conjugates (e.g., RNase conjugates, granzyme antibody-directed enzyme/prodrug therapy), and the like.

Antibody conjugates are also used as diagnostic agents. Antibody diagnostics generally fall within two classes, those for use in in vitro diagnostics, such as in a variety of immunoassays, and those for use in vivo diagnostic protocols, generally known as "antibody-directed imaging" Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, MR hyperpolarized molecules, targeted ultrasound bubbles, and X-ray imaging agents.

The paramagnetic ions contemplated for use as conjugates include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and bismuth (III). Alternative useful isotopes are those used for hyperpolarized MRI, such as carbon-13 and silica-29.

The radioactive isotopes contemplated for use in imaging and radiotherapy as conjugates or covalent incorporation include astatine-211, actinium-225 carbon-14, bismuth-212 chromium-51, chlorine-36, cobalt-57, cobalt-58, copper-64, copper-67, Eu-152, florine-18, gallium-68, gallium-67, gold-198, hydrogen-3, iodine-123, iodine-125, iodine-131, indium-111, iron-52, iron-59, lead-212, lutetium-177, phosphorus-32, rhenium-186, rhenium-188, rubidium-82, rhodium-99, selenium-75, sulphur-35, samarium-153, strontium-92, strontium-89, thallium-201, thorium-227, technetium-94m, technitium-99m, yttrium-86, yttrium-90, zirconium-86, and/or zirconium-89 [PMID: 29545378; PMID: 8679266]. F-18, Zr-89 and Cu-64 often being preferred for PET imaging. Lu-177, At-211, and Yt-90 often being preferred for radiotherapy. Radioactively labeled monoclonal antibodies and antibody fragments of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium-99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups that incorporate chelators, which are often used to bind radioisotopes that exist as metallic ions to an antibody are diethylene-triamine-pentaacetic acid (DTPA), ethylene diamine-tetraacetic acid (EDTA), monomeric or dendrimeric 1,4,7,10-tetraazacyclododecane-1,4,7,10-tetraacetic acid (DOTA), 1,4,7-triazacyclononane-1,4,7-triacetic acid (NOTA), deferoxamine (DFO), or 1-hydroxy-2(1H)-pyridinone derivatives (e.g., 3,4,3-LI(1,2-HOPO) or HOPO).

Exemplary dosing regimens can be found in U.S. Pat. Nos. 5,595,721 and 6,015,542, which are each incorporated herein by reference in their entirety. For example, a radiolabeled antibody may be administered in a single dose designed to deliver a high amount of radioactivity. In such a method, it is contemplated that a radiometric dose of greater than 200 cGy is delivered to the whole body of the patient. In this "high-dose" method, bone marrow transplantation, or some other means of reconstituting hematopoietic function in the patient, is required.

A therapeutic dose of radiolabeled antibody may be administered, however, the radiometric dose received by the patient is limited to a level that toxicity to bone marrow is not significant and reconstitution of hematopoietic function, by bone marrow transplantation or other means, is not required. A range of dose effective in this method is one which delivers between 25 and 200 cGy, preferably 25 to 150 cGy to the whole body of the patient.

Alternatively, a large amount of an unlabelled antibody may be administered to the patient to administration of a therapeutic dose of labelled antibody. This therapeutic dose can be made to deliver a radiometric dose of 5 to 500 cGy, preferably, 25 to 150 cGy, to the whole body of the patient.

A trace-labelled amount of an antibody can be administered to a patient, followed by imaging of the distribution of the antibody in the patient. After imaging, a therapeutic regime of radiolabeled antibody is administered, designed to deliver a radiometric dose of 25 to 500 cGy, preferably 25 to 150 cGy, to the whole body of the patient.

The doses described above are limits for single administrations. Such administrations may be repeated, thus the patient might receive a much higher total accumulated dose over the course of imaging and therapy.

As an example, an amount of radioactivity which would provide approximately 500 cGy to the whole body is estimated to be about 825 mCi of I-131. The amounts of radioactivity to be administered depend, in part, upon the isotope chosen. For therapeutic regimens using 1-131, 5 to 1500 mCi might be employed, with preferable amounts being 5 to 800 mCi, 5 to 250 mCi being most preferable. For Y-90 therapy, 1 to 200 mCi amounts of radioactivity are considered appropriate, with preferable amounts being 1 to 150 mCi, and 1 to 100 mCi being most preferred. The preferred means of estimating tissue doses from the amount of administered radioactivity is to perform an imaging or other pharmacokinetic regimen with a tracer dose, so as to obtain estimates of predicted dosimetry.

A "high-dose" protocol, in the range of 200 to 600 cGy (or higher) to the whole body, typically requires the support of a bone-marrow replacement protocol, as the bone-marrow is the tissue which limits the radiation dosage due to toxicity. A preferable dosage is in the range of 15 to 150 cGy to the whole body, the most preferable range being 40 to 120 cGy. Using such a "low-dose" protocol, toxicity to bone marrow is much lower and we have found complete remissions are achieved without the requirement of bone marrow replacement therapies.

Either or both the diagnostic and therapeutic administrations can be preceded by "pre-doses" of unlabeled antibody. The effects of pre-dosing upon both imaging and therapy have been found to vary from patient to patient. Generally, it is preferable to perform a series of diagnostic imaging administrations, using increasing pre-doses of unlabeled antibody. Then, the pre-dose providing the best ratio of tumor dose to whole body dose is used prior to the administration of the radioimmunotherapeutic dose.

The fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds.

Several methods are known in the art for the attachment or conjugation of an antibody to its conjugate moiety. Some attachment methods involve the use of a metal chelate complex employing, for example, an organic chelating agent such a diethylene-triamine-pentaacetic acid anhydride (DTPA); ethylene-diamine-tetraacetic acid; monomeric or dendrimeric 1,4,7,10-tetraazacyclododecane-1,4,7,10-tetraacetic acid (DOTA); 1,4,7-triazacyclononane-1,4,7-triacetic acid (NOTA); DFO; HOPO; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No.

4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

Another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light. In particular, 2- and 8-azido analogues of purine nucleotides have been used as site-directed photoprobes to identify nucleotide binding proteins in crude cell extracts. The 2- and 8-azido nucleotides have also been used to map nucleotide binding domains of purified proteins and may be used as antibody binding agents.

Derivatization of immunoglobulins by selectively introducing sulfhydryl groups in the Fc region of an immunoglobulin, using reaction conditions that do not alter the antibody combining site are also contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature. This approach has been reported to produce diagnostically and therapeutically promising antibodies which are currently in clinical evaluation.

F. Antibody Drug Conjugates

Antibody drug conjugates, or ADCs, are a new class of highly potent biopharmaceutical drugs designed as a targeted therapy for the treatment of people with disease. ADCs are complex molecules composed of an antibody (a whole mAb or an antibody fragment, such as a scFv) linked, via a stable chemical linker with labile bonds, to a biological active cytotoxic/anti-viral payload or drug. Antibody drug conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the diseased cell so that healthy cells are less severely affected.

In the development of ADC-based anti-tumor therapies, an anticancer drug (e.g., a cell toxin or cytotoxin) is coupled to an antibody that specifically targets a certain cell marker (e.g., a protein that, ideally, is only to be found in or on diseased cells). Antibodies target these proteins in the body and attach themselves to the surface of the diseased cells. The biochemical reaction between the antibody and the target protein (antigen) triggers a signal in the targeted cell, which then absorbs or internalizes the antibody together with the cytotoxin. After the ADC is internalized, the cytotoxic drug is released and kills the cell or impairs cellular replication. In other cases, the linker is cleavable on the surface of the target cell or early endosomes, and as such, full internalization is not required. Due to this targeting, ideally the drug has lower side effects and gives a wider therapeutic window than other agents.

A stable link between the antibody and cytotoxic agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (e.g., anti-cancer) drug. For example, a non-cleavable linker keeps the drug within the cell. As a result, the entire antibody, linker, and cytotoxic agent enter the targeted cell where the antibody is degraded to the level of amino acids. The resulting complex—amino acid, linker and cytotoxic agent—now becomes the active drug. In contrast, cleavable linkers are catalyzed by enzymes in or on the host cell, thereby releasing the cytotoxic agent. Commonly used mechanisms for linker cleavage are protease sensitivity, pH sensitivity, and glutathione sensitivity.

Another type of cleavable linker adds an extra molecule between the cytotoxic drug and the cleavage site. This linker technology allows researchers to create ADCs with more flexibility without worrying about changing cleavage kinetics. Researchers are also developing a new method of peptide cleavage based on Edman degradation. Future direction in the development of ADCs also include the development of site-specific conjugation (TDCs) to further improve stability and therapeutic index and α-emitting immunoconjugates and antibody-conjugated nanoparticles.

G. Intrabodies

In a particular embodiment, the antibody is a recombinant antibody that is suitable for action inside of a cell—such antibodies are known as "intrabodies." These antibodies may interfere with target function by a variety of mechanisms, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required. An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.).

The two major issues impacting the implementation of intrabody therapeutics are delivery, including cell/tissue targeting, and stability. With respect to delivery, a variety of approaches have been employed, such as tissue-directed delivery, use of cell-type specific promoters, viral-based delivery, use of cell-permeability/membrane translocating peptides, and delivery using exosomes. One means of delivery comprises the use of lipid-based nanoparticles, or exosomes, as taught in U.S. Pat. Appln. Publn. 2018/0177727, which is incorporated by reference here in its entirety. With respect to stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

H. Production and Purification of Antibodies

The methods for generating monoclonal antibodies generally begin along the same lines as those for preparing polyclonal antibodies. The first step for both of these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59, and combinations of immunostimulatory molecules ("Adjuvant Systems", such as AS01 or AS03). Additional experimental forms of inoculation to induce antigen-specific B cells are possible, including nanoparticle vaccines, or gene-encoded antigens delivered as DNA or RNA genes in a physical delivery system (such as lipid nanoparticle or on a gold biolistic bead), and delivered with needle, gene gun, or transcutaneous electroporation device. The antigen gene also can be carried as encoded by a replication competent or defective viral vector such as adenovirus, adeno-associated virus, poxvirus, herpesvirus, or alphavirus replicon, or alternatively a virus-like particle.

Methods for generating hybrids of antibody-producing cells and myeloma cells usually comprise mixing somatic cells with myeloma cells in a 2:1 proportion, though the proportion may vary from about 20:1 to about 1:1, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40

Ligand (CD154) in medium containing additional soluble factors, such as IL-21 and human B cell Activating Factor (BAFF), a Type II member of the TNF superfamily Fusion methods using Sendai virus or polyethylene glycol (PEG) are also known. The use of electrically induced fusion methods is also appropriate. Fusion procedures usually produce viable hybrids at low frequencies, about $1\times10^{-6}$ to $1\times10^{-8}$, but with optimized procedures one can achieve fusion efficiencies close to 1 in 200. However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide monoclonal antibodies. The cell lines may be exploited for monoclonal antibody production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide monoclonal antibodies in high concentration. The individual cell lines could also be cultured in vitro, where the monoclonal antibodies are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

Alternatively, a molecular cloning approach may be used to generate monoclonal antibodies. Single B cells labeled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes from single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

Monoclonal antibodies produced by any means may be purified, if desired, using filtration, centrifugation, and various chromatographic methods, such as FPLC or affinity chromatography. Fragments of the monoclonal antibodies of the disclosure can be obtained from the purified monoclonal antibodies by methods that include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

The antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

I. Modification of Antibodies

The sequences of antibodies may be modified for a variety of reasons, such as improved expression, improved cross-reactivity, or diminished off-target binding. Modified antibodies may be made by any technique known to those of skill in the art, including expression through standard molecular biological techniques, or the chemical synthesis of polypeptides.

For example, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

The substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, non-aromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

An amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

An isolated monoclonal antibody, or antigen binding fragment thereof, may contain a substantially homogeneous glycan without sialic acid, galactose, or fucose. The aforementioned substantially homogeneous glycan may be covalently attached to the heavy chain constant region.

A monoclonal antibody may have a novel Fc glycosylation pattern. Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

The isolated monoclonal antibody, or antigen binding fragment thereof, may be present in a substantially homogenous composition represented by the GNGN or G1/G2 glycoform, which exhibits increased binding affinity for Fc gamma RI and Fc gamma RIB compared to the same antibody without the substantially homogeneous GNGN glycoform and with G0, G1F, G2F, GNF, GNGNF or GNG-NFX containing glycoforms. Fc glycosylation plays a significant role in anti-viral and anti-cancer properties of therapeutic mAbs. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, may be expressed in cells that express beta (1,4)-N-acetylglucosaminyltransferase III (GnT III), such that GnT III adds GlcNAc to the antibody. Methods for producing antibodies in such a fashion are provided in WO/9954342 and WO/03011878. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express monoclonal antibodies.

It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding, 10) CD11c/CD18 binding, or
11) Fragmentation Such motifs can be eliminated by altering the synthetic gene comprising the cDNA encoding the antibodies.

Antibodies can be engineered to enhance solubility. For example, some hydrophilic residues such as aspartic acid, glutamic acid, and serine contribute significantly more favorably to protein solubility than other hydrophilic residues, such as asparagine, glutamine, threonine, lysine, and arginine.

B cell repertoire deep sequencing of human B cells from blood donors has been performed on a wide scale. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

J. Characterization of Antibodies

Antibodies according to the present disclosure may be defined, in the first instance, by their binding specificity. Those of skill in the art, by assessing the binding specificity/ affinity of a given antibody using techniques well known to those of skill in the art, can determine whether such antibodies fall within the scope of the instant claims. For example, the epitope to which a given antibody binds may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/
deuterium exchange detected by mass spectrometry. In gen-
eral terms, the hydrogen/deuterium exchange method
involves deuterium-labeling the protein of interest, followed
by binding the antibody to the deuterium-labeled protein.
Next, the protein/antibody complex is transferred to water
and exchangeable protons within amino acids that are pro-
tected by the antibody complex undergo deuterium-to-hy-
drogen back-exchange at a slower rate than exchangeable
protons within amino acids that are not part of the interface.
As a result, amino acids that form part of the protein/
antibody interface may retain deuterium and therefore
exhibit relatively higher mass compared to amino acids not
included in the interface. After dissociation of the antibody,
the target protein is subjected to protease cleavage and mass
spectrometry analysis, thereby revealing the deuterium-
labeled residues which correspond to the specific amino
acids with which the antibody interacts. See, e.g., Ehring
(1999) Analytical Biochemistry 267: 252-259; Engen and
Smith (2001) Anal. Chem. 73: 256A-265A.

The term "epitope" refers to a site on an antigen to which
B and/or T cells respond. B-cell epitopes can be formed both
from contiguous amino acids or noncontiguous amino acids
juxtaposed by tertiary folding of a protein. Epitopes formed
from contiguous amino acids are typically retained on
exposure to denaturing solvents, whereas epitopes formed
by tertiary folding are typically lost on treatment with
denaturing solvents. An epitope typically includes at least 3,
and more usually, at least 5 or 8-10 amino acids in a unique
spatial conformation.

Modification-Assisted Profiling (MAP), also known as
Antigen Structure-based Antibody Profiling (ASAP) is a
method that categorizes large numbers of monoclonal anti-
bodies directed against the same antigen according to the
similarities of the binding profile of each antibody to chemi-
cally or enzymatically modified antigen surfaces (see US
2004/0101920, herein specifically incorporated by reference
in its entirety). Each category may reflect a unique epitope
either distinctly different from or partially overlapping with
epitope represented by another category. This technology
allows rapid filtering of genetically identical antibodies,
such that characterization can be focused on genetically
distinct antibodies. When applied to hybridoma screening,
MAP may facilitate identification of rare hybridoma clones
that produce monoclonal antibodies having the desired char-
acteristics. MAP may be used to sort the antibodies of the
disclosure into groups of antibodies binding different
epitopes.

The present disclosure includes antibodies that may bind
to the same epitope, or a portion of the epitope. One can
easily determine whether an antibody binds to the same
epitope as, or competes for binding with, a reference anti-
body by using routine methods known in the art. For
example, to determine if a test antibody binds to the same
epitope as a reference, the reference antibody is allowed to
bind to target under saturating conditions. Next, the ability
of a test antibody to bind to the target molecule is assessed.
If the test antibody is able to bind to the target molecule
following saturation binding with the reference antibody, it
can be concluded that the test antibody binds to a different
epitope than the reference antibody. On the other hand, if the
test antibody is not able to bind to the target molecule
following saturation binding with the reference antibody,
then the test antibody may bind to the same epitope as the
epitope bound by the reference antibody.

In another aspect, the antibodies may be defined by their
variable sequence, which include additional "framework"

regions. These are provided in Table 4 that represent full
variable regions. Furthermore, the antibodies sequences may
vary from these sequences, optionally using methods dis-
cussed in greater detail below. For example, nucleic acid
sequences may vary from those set out above in that (a) the
variable regions may be segregated away from the constant
domains of the light and heavy chains, (b) the nucleic acids
may vary from those set out above while not affecting the
residues encoded thereby, (c) the nucleic acids may vary
from those set out above by a given percentage, e.g., 70%,
75%, 80%, 85%, 90%, 91%, 92%, 93%, 94%, 95%, 96%,
97%, 98% or 99% homology, (d) the nucleic acids may vary
from those set out above by virtue of the ability to hybridize
under high stringency conditions, as exemplified by low salt
and/or high temperature conditions, such as provided by
about 0.02 M to about 0.15 M NaCl at temperatures of about
50° C. to about 70° C., (e) the amino acids may vary from
those set out above by a given percentage, e.g., 80%, 85%,
90%, 91%, 92%, 93%, 94%, 95%, 96%, 97%, 98% or 99%
homology, or (f) the amino acids may vary from those set out
above by permitting conservative substitutions.

When comparing polynucleotide and polypeptide
sequences, two sequences are said to be "identical" if the
sequence of nucleotides or amino acids in the two sequences
is the same when aligned for maximum correspondence, as
described below. Comparisons between two sequences are
typically performed by comparing the sequences over a
comparison window to identify and compare local regions of
sequence similarity. A "comparison window" as used herein,
refers to a segment of at least about 20 contiguous positions,
usually 30 to about 75, 40 to about 50, in which a sequence
may be compared to a reference sequence of the same
number of contiguous positions after the two sequences are
optimally aligned.

Optimal alignment of sequences for comparison may be
conducted using the Megalign program in the Lasergene
suite of bioinformatics software (DNASTAR, Inc., Madison,
Wis.), using default parameters. Alternatively, optimal align-
ment of sequences for comparison may be conducted by the
local identity algorithm of Smith and Waterman (1981) Add.
APL. Math 2:482, by the identity alignment algorithm of
Needleman and Wunsch (1970) J. Mol. Biol. 48:443, by the
search for similarity methods of Pearson and Lipman (1988)
Proc. Natl. Acad. Sci. USA 85: 2444, by computerized
implementations of these algorithms (GAP, BESTFIT,
BLAST, FASTA, and TFASTA in the Wisconsin Genetics
Software Package, Genetics Computer Group (GCG), 575
Science Dr., Madison, Wis.), or by inspection.

One particular example of algorithms that are suitable for
determining percent sequence identity and sequence simi-
larity are the BLAST and BLAST 2.0 algorithms, which are
described in Altschul et al. (1977) Nucl. Acids Res. 25:3389-
3402 and Altschul et al. (1990) J. Mol. Biol. 215:403-410,
respectively. BLAST and BLAST 2.0 can be used, for
example with the parameters described herein, to determine
percent sequence identity for the polynucleotides and poly-
peptides of the disclosure. Software for performing BLAST
analyses is publicly available through the National Center
for Biotechnology Information. The rearranged nature of an
antibody sequence and the variable length of each gene
requires multiple rounds of BLAST searches for a single
antibody sequence. Also, manual assembly of different
genes is difficult and error-prone. The sequence analysis tool
IgBLAST (world-wide-web at ncbi.nlm.nih.gov/igblast/)
identifies matches to the germline V, D and J genes, details
at rearrangement junctions, the delineation of Ig V domain
framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the antibodies provided herein and their antigen-binding fragments. A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art.

One can determine the biophysical properties of antibodies. One can use elevated temperature to unfold antibodies to determine relative stability, using average apparent melting temperatures. Differential Scanning calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Generally, it is thought that autoreactive clones should be eliminated during ontogeny by negative selection; however, it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

III. Chimeric Antigen Receptors

Chimeric antigen receptor (CAR) molecules are recombinant fusion proteins and are distinguished by their ability to both bind antigen and transduce activation signals via immunoreceptor activation motifs (ITAMs) present in their cytoplasmic tails in order to activate genetically modified immune effector cells for killing, proliferation, and cytokine production. Receptor constructs utilizing an antigen-binding moiety (for example, generated from single chain antibodies (scFv)) afford the additional advantage of being "universal" in that they bind native antigen on the target cell surface in an HLA-independent fashion.

Embodiments of the CARs described herein include nucleic acids encoding an antigen-specific CAR polypeptide comprising an intracellular signaling domain, a transmembrane domain, and an extracellular domain comprising an antigen-binding domain. A CAR may recognize an epitope comprised of the shared space between one or more antigens. Optionally, a CAR can comprise a hinge domain positioned between the transmembrane domain and the antigen binding domain A CAR may further comprise a signal peptide that directs expression of the CAR to the cell surface. For example, a CAR may comprise a signal peptide from GM-CSF. A CAR may also be co-expressed with a membrane-bound cytokine to improve persistence. For example, a CAR may be co-expressed with membrane-bound IL-15.

Depending on the arrangement of the domains of the CAR and the specific sequences used in the domains, immune effector cells expressing the CAR may have different levels activity against target cells. Different CAR sequences may be introduced into immune effector cells to generate engineered cells, the engineered cells selected for elevated SRC, and the selected cells tested for activity to identify the CAR constructs predicted to have the greatest therapeutic efficacy.

A chimeric antigen receptor can be produced by any means known in the art, though preferably it is produced using recombinant DNA techniques. A nucleic acid sequence encoding the several regions of the chimeric antigen receptor can be prepared and assembled into a complete coding sequence by standard techniques of molecular cloning (genomic library screening, PCR, primer-assisted ligation, scFv libraries from yeast and bacteria, site-directed mutagenesis, etc.). The resulting coding region can be inserted into an expression vector and used to transform a suitable expression host allogeneic or autologous immune effector cells, such as a T cell or an NK cell.

The chimeric construct may be introduced into immune effector cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression. Alternatively, a viral vector (e.g., a retroviral vector, adenoviral vector, adeno-associated viral vector, or lentiviral vector) can be used to introduce the chimeric construct into immune effector cells. Suitable vectors for use in accordance with the method of the present invention are non-replicating in the immune effector cells. A large number of vectors are known that are based on viruses, where the copy number of the virus maintained in the cell is low enough to maintain the viability of the cell, such as, for example, vectors based on HIV, SV40, EBV, HSV, or BPV.

A. Antigen Binding Domains

An antigen binding domain may comprise complementarity determining regions of a monoclonal antibody, variable regions of a monoclonal antibody, and/or antigen binding fragments thereof. The antigen binding regions or domains may comprise a fragment of the VH and VL chains of a single-chain variable fragment (scFv) derived from a particular mouse, human, or humanized monoclonal antibody. The fragment can also be any number of different antigen binding domains of an antigen-specific antibody. The fragment may be an antigen-specific scFv encoded by a sequence that is optimized for human codon usage for expression in human cells. In certain aspects, VH and VL domains of a CAR are separated by a linker sequence, such as a Whitlow linker.

The prototypical CAR encodes a scFv comprising VH and VL domains derived from one monoclonal antibody (mAb), coupled to a transmembrane domain and one or more cytoplasmic signaling domains (e.g. costimulatory domains and signaling domains). Thus, a CAR may comprise the LCDR1-3 sequences and the HCDR1-3 sequences of an antibody that binds to B7-H3. In further aspects, however, two of more antibodies that bind to an antigen of interest are identified and a CAR is constructed that comprises: (1) the HCDR1-3 sequences of a first antibody that binds to the antigen; and (2) the LCDR1-3 sequences of a second antibody that binds to the antigen. Such a CAR that comprises HCDR and LCDR sequences from two different antigen binding antibodies may have the advantage of preferential binding to particular conformations of an antigen (e.g., conformations preferentially associated with cancer cells versus normal tissue).

Alternatively, a CAR may be engineered using VH and VL chains derived from different mAbs to generate a panel of CAR+ immune effector cells. The antigen binding domain of a CAR may contain any combination of the LCDR1-3 sequences of a first antibody and the HCDR1-3 sequences of a second antibody.

B. Hinge Domains

A CAR polypeptide may include a hinge domain positioned between the antigen binding domain and the transmembrane domain. In some cases, a hinge domain may be included in CAR polypeptides to provide adequate distance between the antigen binding domain and the cell surface or to alleviate possible steric hindrance that could adversely affect antigen binding or effector function of CAR-modified immune effector cells. The hinge domain may comprise a sequence that binds to an Fc receptor, such as FcγR2a or FcγR1a. For example, the hinge sequence may comprise an Fc domain from a human immunoglobulin (e.g., IgG1, IgG2, IgG3, IgG4, IgA1, IgA2, IgM, IgD or IgE) that binds to an Fc receptor.

A CAR hinge domain may be derived from human immunoglobulin (Ig) constant region or a portion thereof including the Ig hinge, or from human CD8 α transmembrane domain and CD8a-hinge region. A CAR hinge domain may comprise a hinge-$CH_2$—$CH_3$ region of antibody isotype IgG4. The hinge domain (and/or the CAR) may not comprise a wild type human IgG4 CH2 and CH3 sequence. Point mutations may be introduced in antibody heavy chain $CH_2$ domain to reduce glycosylation and non-specific Fc gamma receptor binding of CAR-modified immune effector cells.

A CAR hinge domain may comprise an Ig Fc domain that comprises at least one mutation relative to wild type Ig Fc domain that reduces Fc-receptor binding. For example, the CAR hinge domain can comprise an IgG4-Fc domain that comprises at least one mutation relative to wild type IgG4-Fc domain that reduces Fc-receptor binding. A CAR hinge domain may comprise an IgG4-Fc domain having a mutation (such as an amino acid deletion or substitution) at a position corresponding to L235 and/or N297 relative to the wild type IgG4-Fc sequence. For example, a CAR hinge domain can comprise an IgG4-Fc domain having a L235E and/or a N297Q mutation relative to the wild type IgG4-Fc sequence. A CAR hinge domain may comprise an IgG4-Fc domain having an amino acid substitution at position L235 for an amino acid that is hydrophilic, such as R, H, K, D, E, S, T, N or Q, or that has similar properties to an "E," such as D. A CAR hinge domain may comprise an IgG4-Fc domain having an amino acid substitution at position N297 for an amino acid that has similar properties to a "Q," such as S or T.

The hinge domain may comprise a sequence that is about 85%, 90%, 91%, 92%, 93%, 94%, 95%, 96%, 97%, 98%, 99% or 100% identical to an IgG4 hinge domain, a CD8a hinge domain, a CD28 hinge domain, or an engineered hinge domain.

C. Transmembrane Domains

The antigen-specific extracellular domain and the intracellular signaling-domain may be linked by a transmembrane domain Polypeptide sequences that can be used as part of transmembrane domain include, without limitation, the human CD4 transmembrane domain, the human CD28 transmembrane domain, the transmembrane human CD3ζ domain, a cysteine mutated human CD3ζ domain, or other transmembrane domains from other human transmembrane signaling proteins, such as CD16, CD8, and erythropoietin receptor. For example, the transmembrane domain may comprise a sequence at least 85%, 90%, 91%, 92%, 93%, 94%, 95%, 96%, 97%, 98%, 99% or 100% identical to one of those provided in U.S. Patent Publication No. 2014/0274909 (e.g. a CD8 and/or a CD28 transmembrane domain) or U.S. Pat. No. 8,906,682 (e.g. a CD8a transmembrane domain), both incorporated herein by reference. Transmembrane regions may be derived from (i.e. comprise at least the transmembrane region(s) of) the alpha, beta or zeta chain of the T-cell receptor, CD3 epsilon, CD45, CD4, CD5, CD8, CD9, CD16, CD22, CD33, CD37, CD64, CD80, CD86, CD134, CD137, CD154. In certain specific aspects, the transmembrane domain can be 85%, 90%, 91%, 92%, 93%, 94%, 95%, 96%, 97%, 98%, 99% or 100% identical to a CD8a transmembrane domain or a CD28 transmembrane domain.

D. Intracellular Signaling Domains

The intracellular signaling domain of a CAR is responsible for activation of at least one of the normal effector functions of the immune cell engineered to express the CAR. The term "effector function" refers to a specialized function of a differentiated cell. Effector function of a T cell, for example, may be cytolytic activity or helper activity including the secretion of cytokines. Effector function in a naive, memory, or memory-type T cell includes antigen-dependent proliferation. Thus the term "intracellular signaling domain" refers to the portion of a protein that transduces the effector function signal and directs the cell to perform a specialized function. The intracellular signaling domain may be derived from the intracellular signaling domain of a native receptor. Examples of such native receptors include the zeta chain of the T-cell receptor or any of its homologs (e.g., eta, delta, gamma, or epsilon), MB1 chain, B29, Fc RIII, Fc RI, and combinations of signaling molecules, such as CD3ζ and CD28, CD27, 4-1BB/CD137, ICOS/CD278, IL-2Rβ/CD122, IL-2Rα/CD132, DAP10, DAP12, CD40, OX40/CD134, and combinations thereof, as well as other similar molecules and fragments. Intracellular signaling portions of other members of the families of activating proteins can be used.

While the entire intracellular signaling domain may be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term "intracellular signaling domain" is thus meant to include a truncated portion of the intracellular signaling domain sufficient to transduce the effector function signal, upon CAR binding to a target. One or multiple cytoplasmic domains may be employed, as so-called third generation CARs have at least two or three signaling domains fused together for additive or synergistic effect, for example the CD28 and 4-1BB can be combined in a CAR construct. In certain specific aspects, the intracellular signaling domain comprises a sequence 85%, 90%, 91%, 92%, 93%, 94%, 95%, 96%, 97%, 98%, 99% or 100% identical to a CD3ζ intracellular domain, a CD28 intracellular domain, a CD137 intracellular domain, or a domain comprising a CD28 intracellular domain fused to the 4-1BB intracellular domain.

E. Immune Effector Cells

Immune effectors cells may be T cells (e.g., regulatory T cells, CD4+ T cells, CD8+ T cells, or gamma-delta T cells), natural killer (NK) cells, invariant NK cells, or NKT cells.

Also provided herein are methods of producing and engineering the immune effector cells as well as methods of using and administering the cells for adoptive cell therapy, in which case the cells may be autologous or allogeneic. Thus, the immune effector cells may be used as immunotherapy, such as to target cancer cells.

The immune effector cells may be isolated from subjects, particularly human subjects. The immune effector cells can be obtained from a subject of interest, such as a subject suspected of having a particular disease or condition, a subject suspected of having a predisposition to a particular disease or condition, a subject who is undergoing therapy for a particular disease or condition, a subject who is a healthy volunteer or healthy donor, or from a blood bank Immune effector cells can be collected, enriched, and/or purified from any tissue or organ in which they reside in the subject including, but not limited to, blood, cord blood, spleen, thymus, lymph nodes, bone marrow, tissues removed and/or exposed during surgical procedures, and tissues obtained via biopsy procedures. The isolated immune effector cells may be used directly, or they can be stored for a period of time, such as by freezing.

Tissues/organs from which the immune effector cells are enriched, isolated, and/or purified may be isolated from both living and non-living subjects, wherein the non-living subjects are organ donors Immune effector cells isolated from cord blood may have enhanced immunomodulation capacity, such as measured by CD4- or CD8-positive T cell suppression. The immune effector cells may be isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune effector cell activity. Thus, the cells will be autologous to the subject in need of therapy. Alternatively, the population of immune effector cells can be obtained from a donor, preferably an allogeneic donor. Allogeneic donor cells may or may not be human-leukocyte-antigen (HLA)-compatible. To be rendered subject-compatible, allogeneic cells can be treated to reduce immunogenicity.

1. T Cells

The immune effector cells may be T cells. The T cells may be derived from the blood, bone marrow, lymph, umbilical cord, or lymphoid organs. The T cells may be human T cells. The T cells typically are primary cells, such as those isolated directly from a subject and/or isolated from a subject and frozen. The cells may include one or more subsets of T cells or other cell types, such as whole T cell populations, CD4+ cells, CD8+ cells, and subpopulations thereof, such as those defined by function, activation state, maturity, potential for differentiation, expansion, recirculation, localization, persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. For off-the-shelf technologies, the cells may be derived from pluripotent and/or multipotent cells, such as stem cells, such as induced pluripotent stem cells (iPSCs).

Among the sub-types and subpopulations of T cells (e.g., CD4$^+$ and/or CD8$^+$ T cells) are naive T (T$_N$) cells, effector T cells (T$_{EFF}$), memory T cells and sub-types thereof, such as stem cell memory T (TSC$_M$), central memory T (TC$_M$), effector memory T (T$_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

One or more of the T cell populations may be enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

T cells may be separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into subpopulations by positive or negative selection for markers expressed or expressed to a relatively higher degree on one or more naive, memory, and/or effector T cell subpopulations.

CD8$^+$ T cells may be further enriched for or depleted of naive, central memory, effector memory, and/or central memory stem cells, such as by positive or negative selection based on surface antigens associated with the respective subpopulation. Enrichment for central memory T (T$_{CM}$) cells may be carried out to increase efficacy, such as to improve long-term survival, expansion, and/or engraftment following administration, which in some aspects is particularly robust in such sub-populations.

The T cells may be autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about $2\times10^6$ lymphocytes), e.g., from about 5 to about 21 days, preferably from about 10 to about 14 days.

The cultured T cells can be pooled and rapidly expanded. Rapid expansion provides an increase in the number of antigen-specific T cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as a human leukocyte antigen A2 (HLA-A2) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

The autologous T-cells can be modified to express a T-cell growth factor that promotes the growth and activation of the autologous T-cells. Suitable T-cell growth factors include, for example, interleukin (IL)-2, IL-7, IL-15, and IL-12. Suitable methods of modification are known in the art. See, for instance, Sambrook et al., MOLECULAR CLONING: A LABORATORY MANUAL, 3$^{rd}$ ed., Cold Spring Harbor Press, Cold Spring Harbor, N.Y. 2001; and Ausubel et al., CURRENT PROTOCOLS IN MOLECULAR BIOLOGY, Greene Publishing Associates and John Wiley & Sons, N Y, 1994. In particular aspects, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

2. NK Cells

The immune effector cells may be natural killer (NK) cells. Natural killer (NK) cells are a subpopulation of lymphocytes that have spontaneous cytotoxicity against a variety of tumor cells, virus-infected cells, and some normal cells in the bone marrow and thymus. NK cells are critical effectors of the early innate immune response toward transformed and virus-infected cells. NK cells constitute about 10% of the lymphocytes in human peripheral blood. When lymphocytes are cultured in the presence of interleukin 2 (IL-2), strong cytotoxic reactivity develops. NK cells are effector cells known as large granular lymphocytes because of their larger size and the presence of characteristic azurophilic granules in their cytoplasm. NK cells differentiate and mature in the bone marrow, lymph nodes, spleen, tonsils, and thymus. NK cells can be detected by specific surface markers, such as CD16, CD56, and CD8 in humans. NK cells do not express T-cell antigen receptors, the pan T marker CD3, or surface immunoglobulin B cell receptors.

Stimulation of NK cells is achieved through a cross-talk of signals derived from cell surface activating and inhibitory receptors. The activation status of NK cells is regulated by a balance of intracellular signals received from an array of germ-line-encoded activating and inhibitory receptors. When NK cells encounter an abnormal cell (e.g., tumor or virus-infected cell) and activating signals predominate, the NK cells can rapidly induce apoptosis of the target cell through directed secretion of cytolytic granules containing perforin and granzymes or engagement of death domain-containing receptors. Activated NK cells can also secrete type I cytokines, such as interferon-γ, tumor necrosis factor-α and granulocyte-macrophage colony-stimulating factor (GM-CSF), which activate both innate and adaptive immune cells as well as other cytokines. Production of these soluble factors by NK cells in early innate immune responses significantly influences the recruitment and function of other hematopoietic cells. Also, through physical contacts and production of cytokines, NK cells are central players in a regulatory crosstalk network with dendritic cells and neutrophils to promote or restrain immune responses.

NK cells may be derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. In certain aspects, the NK cells are isolated and expanded ex vivo. For example, CB mononuclear cells may be isolated by ficoll density gradient centrifugation and cultured in a bioreactor with IL-2 and artificial antigen presenting cells (aAPCs). After 7 days, the cell culture may be depleted of any cells expressing CD3 and re-cultured for an additional 7 days. The cells may be again CD3-depleted and characterized to determine the percentage of CD56$^+$/CD3$^-$ cells or NK cells. In other methods, umbilical CB may be used to derive NK cells by the isolation of CD34$^+$ cells and differentiation into CD56$^+$/CD3$^-$ cells by culturing in medium contain SCF, IL-7, IL-15, and IL-2.

F. Engineering of Immune Effector Cells

The immune effectors cells (e.g., autologous or allogeneic T cells (e.g., regulatory T cells, CD4+ T cells, CD8+ T cells, or gamma-delta T cells), NK cells, invariant NK cells, or NKT cells) may be genetically engineered to express antigen receptors such as chimeric antigen receptors (CARs). For example, the host cells (e.g., autologous or allogeneic T-cells) may be modified to express a CAR having antigenic specificity for B7-H3. In particular embodiments, NK cells are engineered to express a CAR. Multiple CARs, such as to different antigens, may be added to a single cell type, such as T cells or NK cells.

The cells may comprise one or more nucleic acids introduced via genetic engineering that encode one or more antigen receptors, and genetically engineered products of such nucleic acids. The nucleic acids may be heterologous, i.e., normally not present in a cell or sample obtained from the cell, such as one obtained from another organism or cell, which for example, is not ordinarily found in the cell being engineered and/or an organism from which such cell is derived. The nucleic acids may not be naturally occurring, such as a nucleic acid not found in nature (e.g., chimeric).

IV. Pharmaceutical Formulations

The present disclosure provides pharmaceutical compositions comprising antibodies that selectively target B7-H3. Such compositions comprise a prophylactically or therapeutically effective amount of an antibody or a fragment thereof and a pharmaceutically acceptable carrier. Also provided herein are pharmaceutical compositions and formulations comprising immune cells (e.g., T cells or NK cells) expressing a CAR and a pharmaceutically acceptable carrier.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The active ingredients can be formulated for parenteral administration, e.g., formulated for injection via the intra-venous, intramuscular, intratumoral, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The pharmaceutical forms suitable for injectable use include sterile aqueous solutions or dispersions; formula-tions including sesame oil, peanut oil, or aqueous propylene glycol; and sterile powders for the extemporaneous prepa-ration of sterile injectable solutions or dispersions. In all cases the form must be sterile and must be fluid to the extent that it may be easily injected. It also should be stable under the conditions of manufacture and storage and must be preserved against the contaminating action of microorgan-isms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, man-delic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formula-tions can include standard carriers such as pharmaceutical grades of mannitol, lactose, starch, magnesium stearate, sodium saccharine, cellulose, magnesium carbonate, etc. Examples of suitable pharmaceutical agents are described in Remington's Pharmaceutical Sciences. Such compositions will contain a prophylactically or therapeutically effective amount of the antibody or fragment thereof, preferably in purified form, together with a suitable amount of carrier so as to provide the form for proper administration to the patient.

Passive transfer of antibodies generally will involve the use of intravenous or intramuscular injections. The forms of antibody can be as monoclonal antibodies. Such immunity generally lasts for only a short period of time, and there is also a potential risk for hypersensitivity reactions, and serum sickness, especially from gamma globulin of non-human origin. The antibodies will be formulated in a carrier suitable for injection, i.e., sterile and syringeable.

Generally, the ingredients of compositions of the disclo-sure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle con-taining sterile pharmaceutical grade water or saline. Where the composition is administered by injection, an ampoule of sterile water for injection or saline can be provided so that the ingredients may be mixed prior to administration.

In certain embodiments, pharmaceutical compositions may comprise, for example, at least about 0.1% of an active ingredient. In other embodiments, an active ingredient may comprise between about 2% to about 75% of the weight of the unit, or between about 25% to about 60%, for example, and any range derivable therein.

The term "unit dose" or "dosage" refers to physically discrete units suitable for use in a subject, each unit con-taining a predetermined quantity of the therapeutic compo-sition calculated to produce the desired responses discussed above in association with its administration, i.e., the appro-priate route and treatment regimen. The quantity to be administered, both according to number of treatments and unit dose, depends on the effect desired. The actual dosage amount of a composition of the present embodiments admin-istered to a patient or subject can be determined by physical and physiological factors, such as body weight, the age, health, and sex of the subject, the type of disease being treated, the extent of disease penetration, previous or con-current therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentra-tion of active ingredient(s) in a composition and appropriate dose(s) for the individual subject.

V. Methods of Treatment

Certain aspects of the present embodiments can be used to prevent or treat a disease or disorder associated with elevated levels of B7-H3, such as cancer, such as renal, pancreatic, colorectal, non-small cell lung, ovarian, bladder, melanoma, prostate, and neuroectodermal cancer. Functioning of B7-H3 may be reduced by any suitable drugs. Preferably, such substances would be an anti-B7-H3 antibody, an anti-B7-H3 antibody-drug conjugate, B7-H3-specific CAR T cell, or B7-H3-specific CAR NK cell.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that targets B7-H3, either alone or in combination with administration of chemotherapy, immunotherapy, or radiotherapy, performance of surgery, or any combination thereof.

The term "subject" as used herein refers to any individual or patient to which the subject methods are performed. Generally, the subject is human, although as will be appreciated by those in the art, the subject may be an animal. Thus, other animals, including mammals, such as rodents (including mice, rats, hamsters, and guinea pigs), cats, dogs, rabbits, farm animals (including cows, horses, goats, sheep, pigs, etc.), and primates (including monkeys, chimpanzees, orangutans, and gorillas) are included within the definition of subject.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "cancer," as used herein, may be used to describe a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma;

papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, a neurodegenerative disease, and/or a genetic disorder).

In certain embodiments, the compositions and methods of the present embodiments involve an antibody or an antibody fragment against B7-H3, in combination with a second or additional therapy, such as chemotherapy or immunotherapy. Such therapy can be applied in the treatment of any disease that is associated with elevated B7-H3. For example, the disease may be a cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, immunotherapy, or radioimmunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, to induce chromosomal and mitotic aberrations by affecting nucleic acid synthesis. Alternatively, an agent may inhibit a specific enzyme activity in the cell, e.g., inhibit a kinase, a phosphatase, a lipase, a methyltransferase, an ethyl-transferase, a dioxygenase, or alternatively, the agent may block hormone activity, inhibit signal transduction, modify gene expression, induce apoptosis, or inhibit angiogenesis, or the agent may comprise a cancer vaccine or gene therapy.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegal1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, uben-

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | | imex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diazi-quone; elformithine; elliptinium acetate; an epothilone; eto-glucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cis-platin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylor-nithine (DMFO); retinoids, such as retinoic acid; capecitabine; carboplatin, procarbazine, plicomycin, gemcitabien, navelbine, farnesyl-protein tansferase inhibi-tors, transplatinum, and pharmaceutically acceptable salts, acids, or derivatives of any of the above.

Alternatively, any of a variety of molecularly targeted therapeutic agents may be used in accordance with the present embodiments. Examples include but are not limited to tyrosine kinase inhibitor (TKIs), PARP1/2 inhibitors, angiogenesis inhibitors, hormone blockers, gene expression modulators, epigenetic modifiers, and signal transduction inhibitors.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradia-tion. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating mol-ecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investiga-tion or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and mono-clonal antibodies, e.g., anti-CD20, anti-ganglioside GM2, and anti-p185 (Hollander, 2012; Hanibuchi et al., 1998; U.S. Pat. No. 5,824,311). Alternatively, blocking "don't eat me" signals (CD24) on tumor cells represents another strategy [PMID: 31367043]. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal Immune checkpoint proteins that may be targeted by immune checkpoint blockade include adenosine A2A receptor (A2AR), B7-H3 (also known as CD276), B and T lymphocyte attenuator (BTLA), CCL5, CD27, CD38, CD8A, CMKLR1, cytotoxic T-lymphocyte-associated pro-tein 4 (CTLA-4, also known as CD152), CXCL9, CXCR5, glucocorticoid-induced tumour necrosis factor receptor-re-lated protein (GITR), HLA-DRB1, ICOS (also known as CD278), HLA-DQA1, HLA-E, indoleamine 2,3-dioxy-genase 1 (IDO1), killer-cell immunoglobulin (KIR), lym-phocyte activation gene-3 (LAG-3, also known as CD223), Mer tyrosine kinase (MerTK), NKG7, OX40 (also known as CD134), programmed death 1 (PD-1), programmed death-ligand 1 (PD-L1, also known as CD274), PDCD1LG2, PSMB10, STAT1, T cell immunoreceptor with Ig and ITIM domains (TIGIT), T-cell immunoglobulin domain and mucin domain 3 (TIM-3), and V-domain Ig suppressor of T cell activation (VISTA, also known as C10orf54). In particular, the immune checkpoint inhibitors target the PD-1 axis and/or CTLA-4.

The immune checkpoint inhibitors may be drugs, such as small molecules, recombinant forms of ligand or receptors, or antibodies, such as human antibodies (e.g., International Patent Publication WO2015/016718; Pardoll, *Nat Rev Cancer,* 12(4): 252-264, 2012; both incorporated herein by reference). Known inhibitors of the immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide. Anti-human-CTLA-4 antibodies (or VH and/ or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675, 206, also known as tremelimumab; formerly ticilimumab); U.S. Pat. No. 6,207,156; Hurwitz et al. (1998) *Proc Natl Acad Sci USA,* 95(17): 10067-10071; Camacho et al. (2004) *J Clin Oncology,* 22(145): Abstract No. 2505 (antibody CP-675206); and Mokyr et al. (1998) *Cancer Res,* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP-002277. LAG-3 is found on the surface of activated T cells, natural killer cells, B cells, and plasmacytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTAS antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another metabolic protein with immune function that can be targeted in the methods provided herein is indoleamine 2,3-dioxygenase (IDO). The complete protein sequence of human IDO has Genbank accession number NP_002155. In some embodiments, the immune inhibitor is a small molecule IDO inhibitor. Exemplary small molecules include BMS-986205, epacadostat (INCB24360), and navoximod (GDC-0919).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Another immune checkpoint protein that can be targeted in the methods provided herein is OX40, also known as CD134. The complete protein sequence of human OX40 has Genbank accession number NP_003318. In some embodiments, the immune checkpoint inhibitor is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another immune checkpoint protein that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immune checkpoint inhibitor is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

In some embodiments, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering (Park, Rosenberg et al. 2011). Isolation and transfer of tumor specific T cells has been shown to be successful in treating melanoma. Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lympho-mas and solid tumors (Jena, Dotti et al. 2010).

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

D. Surgery

Approximately 60% of persons with cancer will undergo surgery of some type, which includes preventative, diagnos-tic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radio-therapy, hormonal therapy, gene therapy, immunotherapy, and/or alternative therapies. Tumor resection refers to physi-cal removal of at least part of a tumor. In addition to tumor resection, treatment by surgery includes laser surgery, cryo-surgery, electrosurgery, and microscopically-controlled sur-gery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodi-ments to improve the therapeutic efficacy of treatment. These additional agents include agents that affect the upregulation of cell surface receptors and GAP junctions, cytostatic and differentiation agents, inhibitors of cell adhe-sion, agents that increase the sensitivity of the hyperprolif-erative cells to apoptotic inducers, or other biological agents. Increases in intercellular signaling by elevating the number of GAP junctions would increase the anti-hyperproliferative effects on the neighboring hyperproliferative cell popula-tion. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodi-ments. Examples of cell adhesion inhibitors are focal adhe-sion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

VI. Methods of Detection

In some aspects, the present disclosure concerns immu-nodetection methods for detecting expression of B7-H3. A wide variety of assay formats are contemplated for detecting protein products, including immunohistochemistry, enzyme linked immunosorbent assay (ELISA), radioimmunoassay (RIA), immunoradiometric assay, fluoroimmunoassay, chemiluminescent assay, bioluminescent assay, dot blotting, FACS analyses, mass cytometry (CyTOF), imaging mass cytometry (IMC), and Western blot to mention a few. The steps of various useful immunodetection methods have been described in the scientific literature. In general, the immu-nobinding methods include obtaining a sample, and contact-ing the sample with an antibody specific for the protein to be detected, as the case may be, under conditions effective to allow the formation of immunocomplexes. In general, the detection of immunocomplex formation is well known in the art and may be achieved through the application of numer-ous approaches. These methods are generally based upon the detection of a label or marker, such as any of those radio-active, metallic, fluorescent, biological and enzymatic tags. The detection methods may involve imaging ex vivo, such as CyTOF or IMC. Alternatively, the detection methods may involve imaging in vivo, such as PET or SPECT imaging. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

In some aspects, the present disclosure provides methods of imaging using the compounds and compositions of the present disclosure. In some embodiments, the imaging is positron-emission tomography. Positron emission tomogra-phy (PET) imaging is based on detecting two time-coinci-dent high-energy photons from the emission of a positron-emitting radioisotope. PET imaging is unique in its very high sensitivity and accurate estimation of the in vivo concentration of the radiotracer. PET imaging has been widely adopted as an important clinical modality for onco-logical, cardiovascular, and neurological applications. PET imaging has also become an important tool in preclinical studies, particularly for investigating murine models of disease and other small-animal models.

As used herein, the term "sample" refers to any sample suitable for the detection methods provided by the present invention. The sample may be any sample that includes material suitable for detection or isolation. Sources of samples include blood, pleural fluid, peritoneal fluid, urine, saliva, malignant ascites, broncho-alveolar lavage fluid, synovial fluid, and bronchial washes. In one aspect, the sample is a blood sample, including, for example, whole blood or any fraction or component thereof. A blood sample suitable for use with the present invention may be extracted from any source known that includes blood cells or com-ponents thereof, such as venous, arterial, peripheral, tissue, cord, and the like. For example, a sample may be obtained and processed using well-known and routine clinical meth-ods (e.g., procedures for drawing and processing whole blood). In one aspect, an exemplary sample may be periph-eral blood drawn from a subject with cancer. In some aspects, the biological sample comprises a plurality of cells.

In certain aspects, the biological sample comprises fresh or frozen tissue. In specific aspects, the biological sample comprises formalin fixed, paraffin embedded tissue. In some aspects, the biological sample is a tissue biopsy, fine needle aspirate, blood, serum, plasma, cerebral spinal fluid, urine, stool, saliva, circulating tumor cells, exosomes, or aspirates and bodily secretions, such as sweat. In some aspects, the biological sample contains cell-free DNA.

VII. Formulations and Routes of Administration

In another aspect, for administration to a patient in need of diagnostic evaluation and/or treatment, radiopharmaceutical formulations (also referred to as radiopharmaceutical preparations, radiopharmaceutical compositions, radiopharmaceuticals, or radiopharmaceutical products) comprise a diagnostically or therapeutically effective amount of a radiolabeled compound disclosed herein formulated with one or more excipients and/or drug carriers appropriate to the indicated route of administration.

In some embodiments, the radiolabeled compounds disclosed herein are formulated in a manner amenable for diagnostic evaluation or treatment of human and/or veterinary subjects. In some embodiments, formulation comprises admixing or combining one or more of the radiolabeled compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Radiopharmaceutical formulations may be administered by a variety of methods, such as by injection (e.g., subcutaneous, intravenous, intratumoral, and intraperitoneal). Depending on the route of administration, the radiolabeled compounds disclosed herein may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes. The radiolabeled compounds disclosed herein may also be administered parenterally, intraperitoneally, intratumorally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Radiopharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of radiopharmaceutical calculated to produce the desired imaging effect in association with the required pharmaceutical carrier. In some embodiments, the specification for the dosage unit forms of the disclosure are dictated by and directly dependent on (a) the unique characteristics of the radiopharmaceutical and the particular imaging effect to be achieved, and (b) the limitations inherent in the art of compounding such a radiopharmaceutical for the imaging of a patient. In some embodiments, active compounds are administered at an effective dosage sufficient to produce a PET image of immune activity in a patient. For example, the efficacy of a compound can be evaluated in an animal model system that may be predictive of efficacy in imaging immune activity in a human or another animal.

VIII. Kits

In various aspects of the embodiments, a kit is envisioned containing therapeutic agents and/or other therapeutic and delivery agents. In some embodiments, kits are provided for preparing and/or administering a therapy of the embodiments. The kit may comprise one or more sealed vials containing any of the pharmaceutical compositions of the present embodiments. The kit may include, for example, at least one B7-H3 antibody or B7-H3-specific CAR construct, as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

IX. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Generation of Therapeutic Antibodies Targeting B7-H3

New Zealand Black/White F1 hybrid mice (NZBWF1/J, Jackson Labs, stock no 100008) were used to generate antibodies against B7-H3. NZBW mice are widely used as a model for autoimmune diseases resembling human systemic lupus erythematosus, rendering elevated levels of immunoglobulin, anti-nuclear antibodies, anti-thymocyte antibodies, and severe progressive glomerulonephritis. These auto-immune characteristics arise from defects in self-tolerance. Here, the broken tolerance to auto-antigens in the NZBWF1/J strain was exploited by vaccinating the animals with an appropriate source comprising cells that express both murine and human B7-H3, wherein candidate murine auto-antibodies against B7-H3 epitopes or bio-similars would not be eliminated by host immune processing.

Thus, there was an enhanced probability that a high-affinity monoclonal antibody reactive to both human (foreign) and murine (self) epitopes would be recovered from the serum.

Murine L cells (ATCC) were engineered to express human 4Ig-B7-H3 on their cell surface, in addition to native murine 2Ig-B7-H3, by transduction with a custom lentivirus encoding human 4Ig-B7-H3 (GeneCopoeia, Inc.). Six inoculations of whole cells, $10 \times 10^6$ cells/inoculation, into NZBWF1/J mice yielded 1,440 hybridoma clones. Screening yielded 14 candidate hybridoma cell lines found to bind to 4Ig-B7-H3 L cells by standard ELISA immune screening. Of these candidates, secondary testing of supernatants against HeLa cells (that express high levels of human 4Ig-B7-H3) resulted in one high affinity candidate. After expansion and antibody purification, further analysis by biolayer interferometry resulted in the discovery and characterization of MIL33B, as a candidate with pM affinity to human 4Ig-B7-H3 and nM affinity to murine 2Ig-B7-H3.

A MIL33B hybridoma pellet was frozen and sent to a sequencing core facility (Vanderbilt Sequencing Center, Nashville, TN) for sequencing of the hypervariable regions of both the heavy and light chains. The isotype of MIL33B has been determined to be IgG2a. The complementarity-determining regions (CDR) and variable regions of the MIL33B antibody are provided in Tables 1-3.

TABLE 1

CDRs of variable sequences of the MIL33B antibody as predicted by IMGT/DomainGapAlign (Ehrenmann et al., 2010; Ehrenmann & Lefranc, 2011).

| Chain | CDR1 (SEQ ID NO:) | CDR2 (SEQ ID NO:) | CDR3 (SEQ ID NO:) |
|---|---|---|---|
| Heavy | GYTFTSYV (SEQ ID NO: 1) | INSYSDGT (SEQ ID NO: 2) | ARWGGLGNGAMDY (SEQ ID NO: 3) |
| Light | SSVNY (SEQ ID NO: 4) | DTS (SEQ ID NO: 5) | QQWTSNPLT (SEQ ID NO: 6) |

TABLE 2

CDRs of variable sequences of the MIL33B antibody as predicted by Paratome (Kunik et al., 2012a; Kunik et al., 2012b).

| Chain | CDR1 (SEQ ID NO:) | CDR2 (SEQ ID NO:) | CDR3 (SEQ ID NO:) |
|---|---|---|---|
| Heavy | YTFTSYVMH (SEQ ID NO: 11) | GIGYINSYSDGTKY (SEQ ID NO: 12) | RWGGLGNGAMDY (SEQ ID NO: 13) |
| Light | SSVNYMH (SEQ ID NO: 14) | RWIYDTSKLAS (SEQ ID NO: 15) | QQWTSNPL (SEQ ID NO: 16) |

TABLE 3

CDRs of variable sequences of the MIL33B antibody as predicted by Chothia.

| Chain | CDR1 (SEQ ID NO:) | CDR2 (SEQ ID NO:) | CDR3 (SEQ ID NO:) |
|---|---|---|---|
| Heavy | GYTFTSY (SEQ ID NO: 17) | NSYSDG (SEQ ID NO: 18) | WGGLGNGAMD (SEQ ID NO: 19) |
| Light | SVSSSVNYMH (SEQ ID NO: 20) | DTSKLAS (SEQ ID NO: 21) | QQWTSNPLT (SEQ ID NO: 6) |

TABLE 4

| Protein sequences for the MIL33B variable regions. | | |
|---|---|---|
| Chain | Variable Sequence | SEQ ID NO: |
| Heavy | EVQLQQSGPELVKPGASVKMSCKASGYTFTSYVMHWVRQSPGQGLE GIGYINSYSDGTKYNEKFKGKATLTSDKSSSTAYMELSGLTSEDSA VYYCARWGGLGNGAMDYWGQGTSVTVSS | 7 |
| Light | QIVLTQSPAIMSASPGEKVTMTCSVSSSVNYMHWYQQKSGTSPKRW IYDTSKLASGVPARFSASGSGTSYSLTISSMEAEDAATYYCQQWTS NPLTFGAGTKLELK | 8 |

TABLE 5

| Nucleotide sequences for the MIL33B variable regions. | | |
|---|---|---|
| Chain | Variable Sequence | SEQ ID NO: |
| Heavy | GAGGTCCAGCTGCAGCAGTCTGGACCTGAGCTGGTAAAGCCTGGGG CTTCAGTGAAGATGTCCTGCAAGGCTTCTGGATACACATTCACTAG CTATGTCATGCACTGGGTGAGGCAGAGCCCTGGGCAGGGCCTTGAG GGGATTGGATATATTAATTCTTACAGTGATGGAACTAAGTACAATG AGAAGTTCAAAGGCAAGGCCACACTGACTTCAGACAAATCCTCCAG CACAGCCTACATGGAGCTCAGCGGCCTGACCTCTGAGGACTCTGCG GTCTATTACTGTGCAAGATGGGGAGGATTAGGAAATGGCGCTATGG ACTACTGGGGTCAAGGAACCTCAGTCACCGTCTCCTCA | 9 |
| Light | CAAATTGTTCTCACCCAGTCTCCAGCAATCATGTCTGCATCTCCAG GGGAGAAGGTCACCATGACCTGCAGTGTCAGCTCAAGTGTAAATTA CATGCACTGGTACCAGCAGAAGTCAGGCACCTCCCCCAAAAGATGG ATTTATGACACATCCAAACTGGCTTCTGGAGTCCCTGCTCGCTTCA GTGCCAGTGGGTCTGGGACCTCTTACTCTCTCACAATCAGCAGCAT GGAGGCTGAAGATGCTGCCACTTATTACTGCCAGCAGTGGACTAGT AACCCGCTCACGTTCGGTGCTGGGACCAAGCTGGAGCTGAAA | 10 |

Example 2—MIL33B Binds Human 4Ig-B7-H3 with pM Affinity

Figure 1:
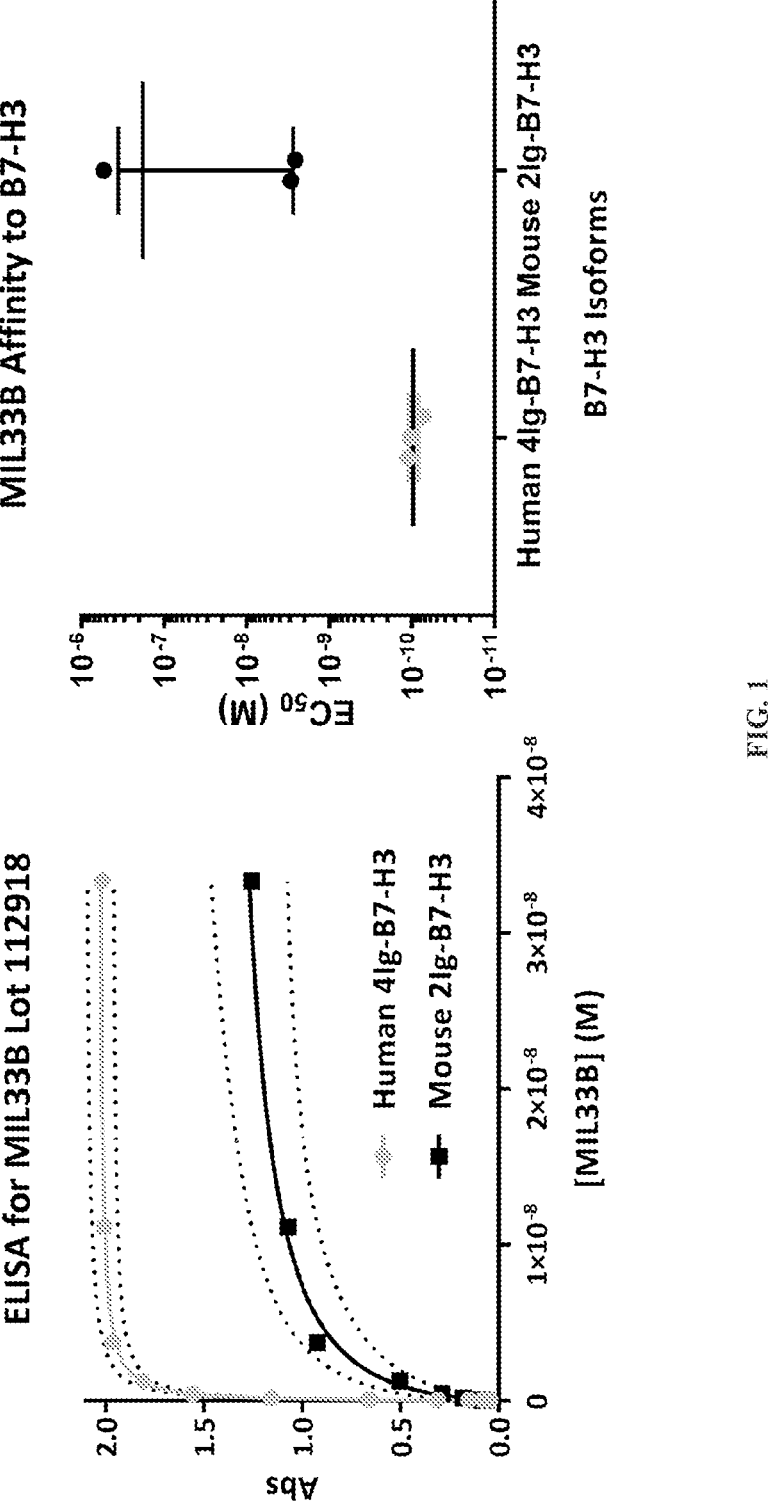
FIG. 1. ELISA for binding of MIL33B to human 4Ig-B7-H3 and mouse 2Ig-B7-H3.

The in vitro binding affinity of MIL33B for human 4Ig-B7-H3 and mouse 2Ig-B7-H3 was assessed by ELISA. The extracellular domains of human 4Ig-B7-H3 and murine 2Ig-B7-H3 were purchased and plated down onto 96-well plates. The plates were then incubated with varying concentrations of purified MIL33B. Plates were then washed and assessed for antibody binding through absorbance measurements. This experiment was completed for three independent productions and purifications of MIL33B. The EC50 for each curve for each lot was calculated and plotted (log plot) (FIG. 1). MIL33B has picomolar affinity for human 4Ig-B7-H3 and nanomolar affinity for mouse 2Ig-B7-H3.

Example 3—MIL33B Selectively Binds to Human 4Ig-B7-H3

Figure 2:
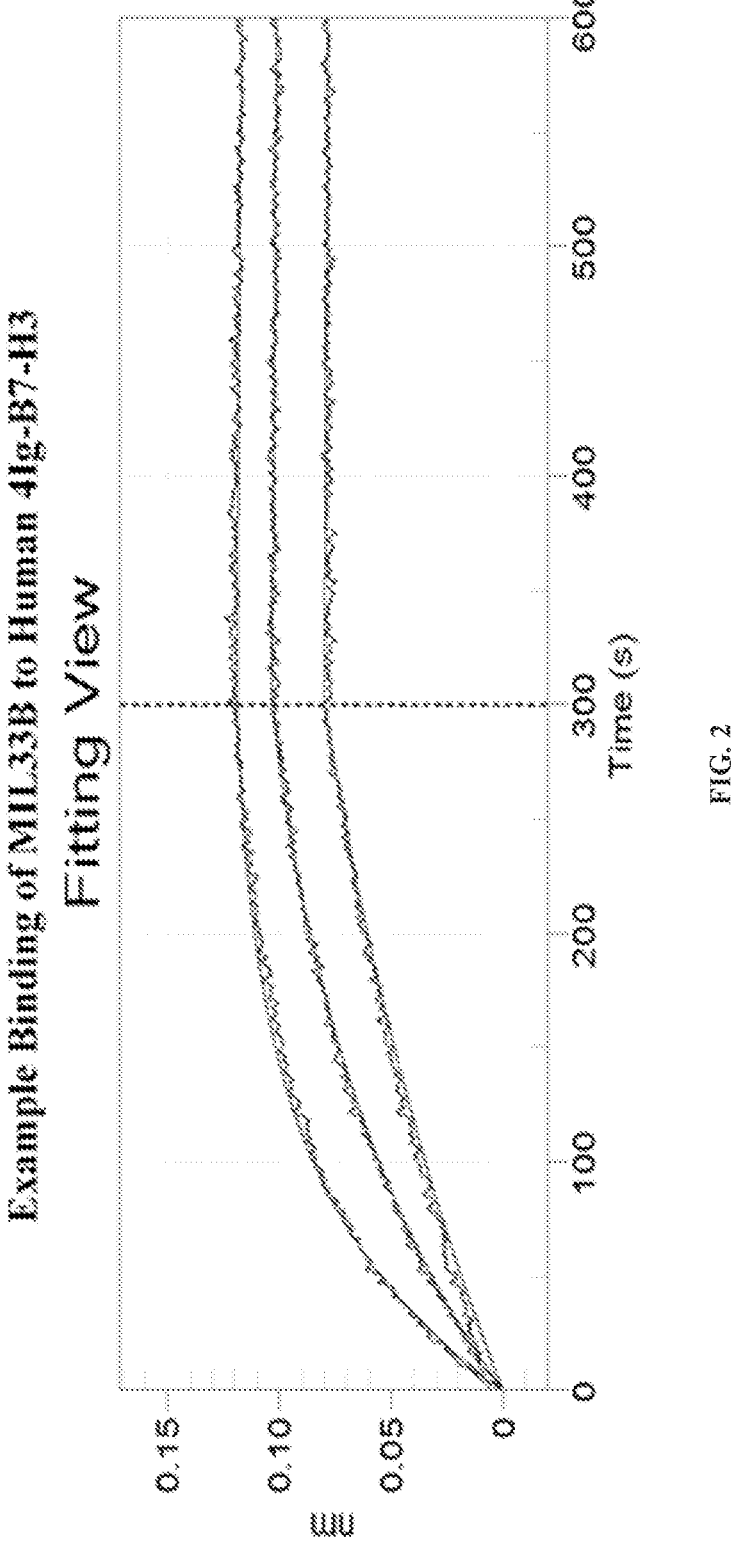
FIG. 2. Example binding of MIL33B to human 4Ig-B7-H3. Dissociation constants, Kd, were determined utilizing biolayer interferometry (Octet) assays. MIL33B was captured onto the surface of the optical sensor. The surface is then placed into a solution of analyte and the phase shift indicating binding was measured over time. The probe was then moved into a solution without analyte and the time course of off-binding was measured. This cycle was repeated for multiple analyte concentrations, and the Kd was calculated from global curve fitting of the concentration- and time-dependence of the analyte binding to the antibody.

The extracellular domains of the indicated B7 family proteins were purchased from R&D Systems. All proteins were validated by the vendor to be both pure and functional. Kd values were determined utilizing capture biolayer interferometry (Octet, Molecular Devices) in "affinity" mode, wherein the MIL33B antibody was captured on the tip of the probe and placed into solutions containing different concentrations of target extracellular domain. Kd, Kd error, and $R^2$ values are reported in Table 6. An exemplary fitting view of the binding of MIL33B to human 4Ig-B7-H3 is shown in FIG. 2. These data show that MIL33B binds to 4Ig-B7-H3 at least 1000-fold better than to other B7 family members.

TABLE 6

| Binding of MIL33B to various B7 family members. | | | |
|---|---|---|---|
| Protein Target | Kd (M) | Kd Error (M) | $R^2$ |
| Human 4Ig-B7-H3 | 7.23E−11 | 5.96E−12 | 0.9962 |
| Human 2Ig-B7-H3 | 5.8E−10 | 5.17E−11 | 0.9532 |
| Mouse 2Ig-B7-H3 | 4.11E−08 | 2.98E−09 | 0.93 |
| Human B7-H1 | >1.0E−6 | 1.15E−07 | 0 |
| Mouse B7-H1 | >1.0E−6 | 1.15E−07 | 0 |
| Human PD-1 | >1.0E−6 | 1.15E−07 | 0 |
| Mouse PD-1 | >1.0E−6 | 1.24E−08 | 0 |
| Human PD-L2 | >1.0E−6 | 3.77E−08 | 0 |
| Mouse PD-L2 | >1.0E−6 | 4.52E−09 | 0 |
| Human B7-H2 | >1.0E−6 | 1.0E−12 | 0 |
| Mouse B7-H2 | >1.0E−6 | 4.19E−09 | 0 |
| Human B7-H4 | >1.0E−6 | 5.78E−16 | 0 |
| Mouse B7-H4 | >1.0E−6 | 2.21E−11 | 0 |

Figure 3:
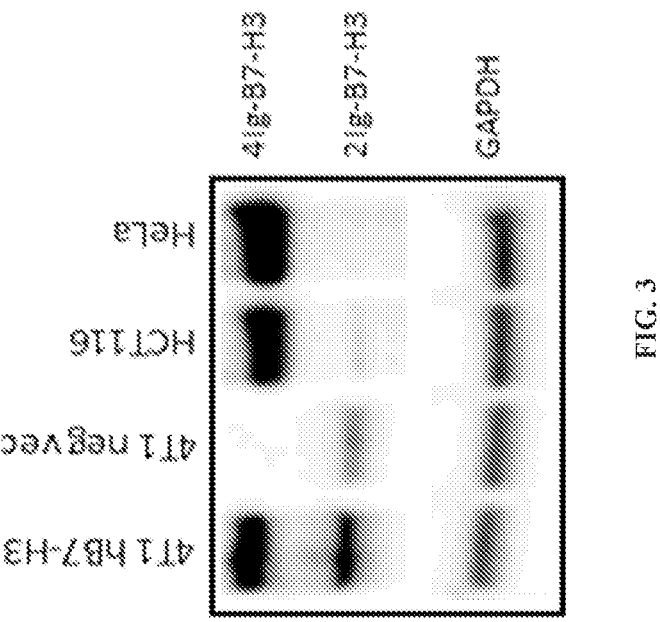
FIG. 3. Western blot of human 4Ig-B7-H3 and mouse 2Ig-B7-H3 expression in various cell lines.

Example 4—Fluorescently Labeled MIL33B Selectively Binds to B7-H3-Expressing Cells Vs Isotype Control MIL33B labeled with Alexa594 fluorophore was used in live cell immuno-fluorescence microscopy to demonstrate selective, blockable binding to both human and murine B7-H3 expressed on tumor cells. Murine breast tumor, 4T1 cells (ATCC), were stably transduced with human 4Ig-B7-H3 or empty vector using lentiviral constructs. Cells were selected that demonstrated levels of 4Ig-B7-H3 expression that matched those found endogenously in human solid tumors known to express B7-H3, such as cervical cancer (HeLa) or colorectal cancer (HCT 116) (FIG. 3). These engineered cells provide relevant models.

MIL33B or isotype control IgG2a were labeled with Alexa594 fluorophore utilizing commercially available kits (Life Technologies) at 1 mg/mL and purified via size exclusion column. The resulting products were designated MIL33B-A594 or IgG2a-A594. Labeling yields were quantified via UV/Vis spectrometry.

Figure 4A:
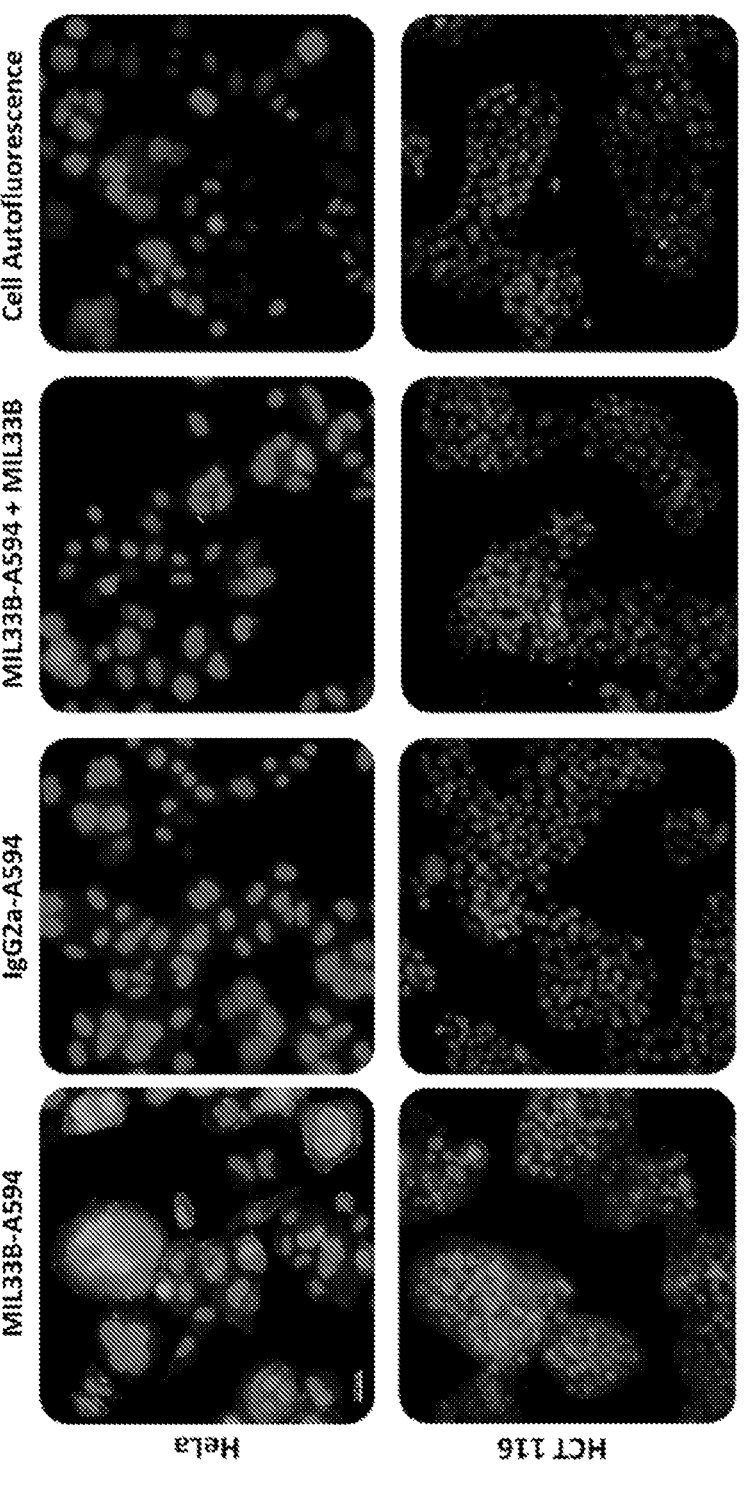
FIGS. 4A-C. Binding of Alexa594-labeled MIL33B and Alexa594-labeled isotype control IgG2a to cells expressing 4Ig-B7-H3 and/or 2Ig-B7-H3.

Cells expressing human 4Ig-B7-H3 were incubated either alone, with labeled MIL33B (1 μg/mL) or murine isotype control IgG2a (1 μg/mL) for 1 hr at 37° C. Blocking experiments were conducted by incubating cells with unlabeled MIL33B at 50 μg/mL prior to addition of MIL33B-A594 at 1 μg/mL. Cells were washed and imaged by fluorescence microscopy (TiE, Nikon). Antibody binding (red) was co-registered with nuclear staining (blue) (FIGS. 4A&B).

Figures 4B, 4C:
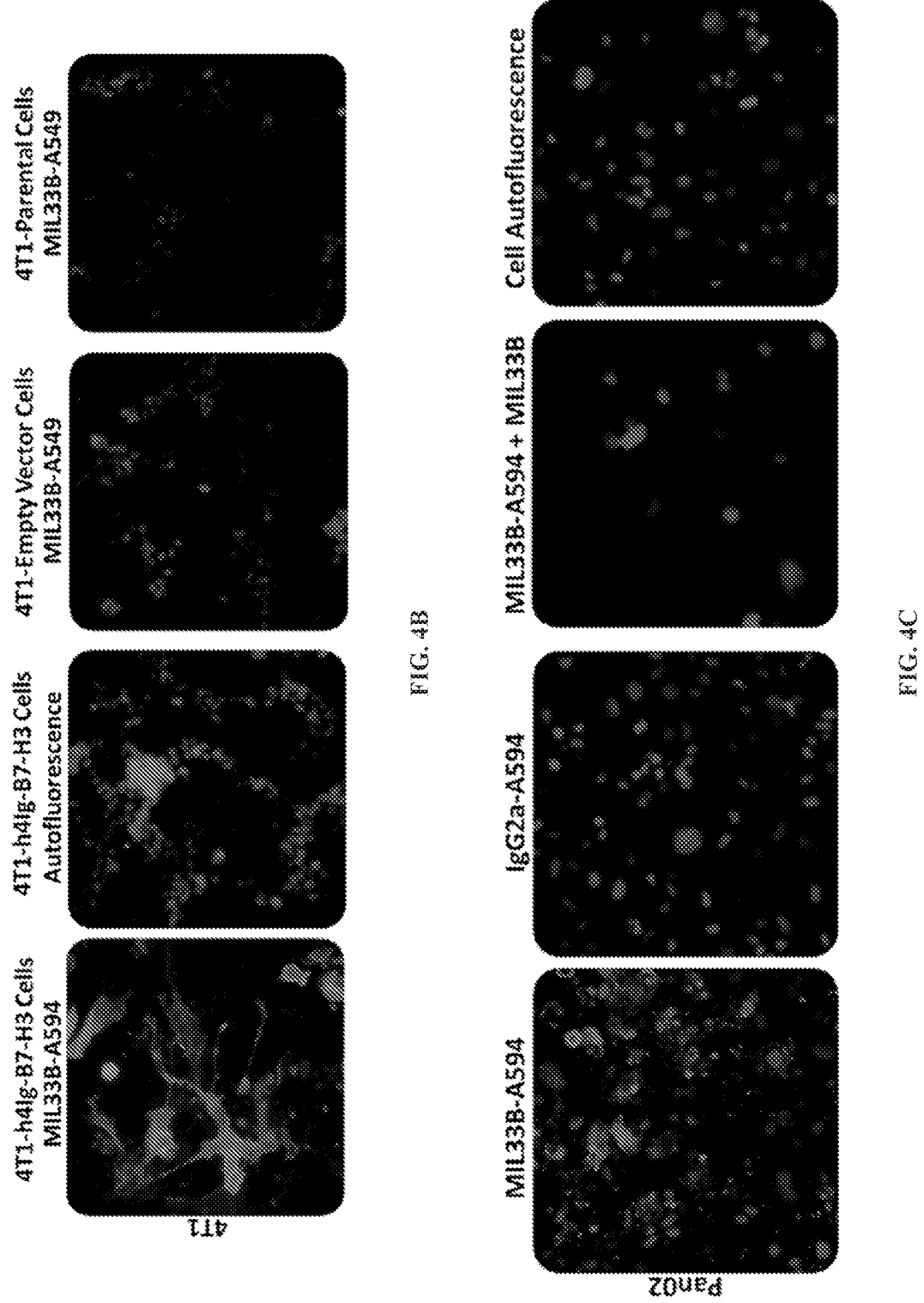

Pan02 cells, a pancreatic tumor of murine origin known to express murine 2Ig-B7-H3, were similarly imaged with MIL33B-A594 using 100 μg/mL of MIL33B-A594, reflecting the ~100-fold shift in Kd from human 4Ig-B7-H3 to murine 2Ig-B7-H3 (FIG. 4C).

Example 5—Flagellin-Conjugated MIL33B Induces the NF-κB Pathway Via TLR5

MIL33B conjugated to the TLR5 agonist, flagellin, maintained nM binding affinity and was capable of inducting inflammatory pathways, such as NF-κB via TLR5, in live cell assays.

Figure 5:
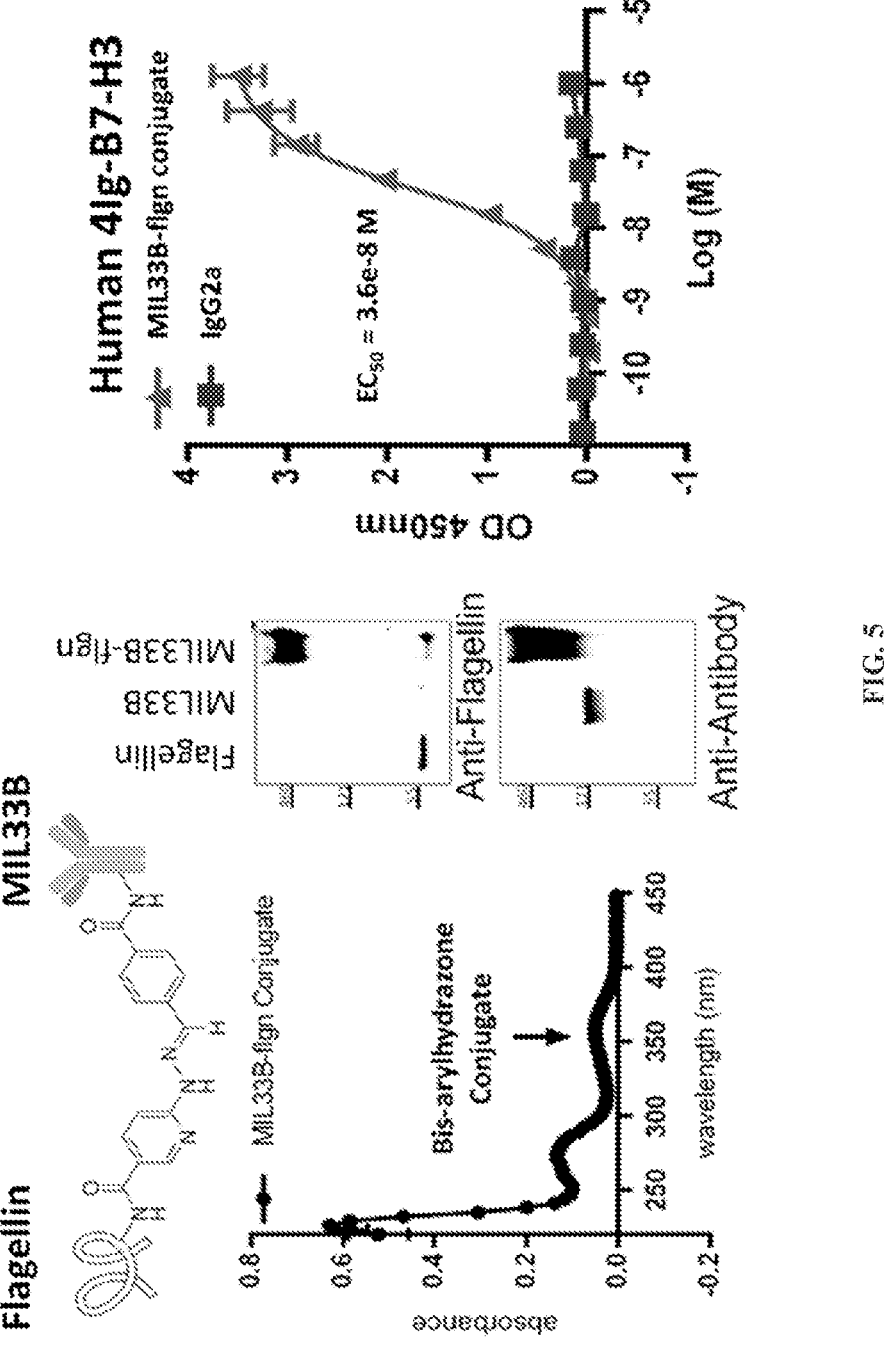
FIG. 5. Conjugation of MIL33B to flagellin, confirmed by Western blot, and affinity analysis thereof for binding to human 4Ig-B7-H3.

Purified flagellin (InvivoGen) was conjugated to MIL33B through a commercially available linker kit (see diagram). Conjugation was verified through UV-Vis spectrometry, and dual Western blots confirmed >90% of the antibody was conjugated to a higher molecular weight species and that species also contained flagellin (FIG. 5). A loss of affinity is expected upon conjugation of antibodies to ligands. Due to the initial pM affinity of the antibody, the conjugate still maintained 36 nM EC50 to human 4Ig-B7-H3 after conjugating to flagellin as determined by ELISA (FIG. 5, right panel).

Figure 6:
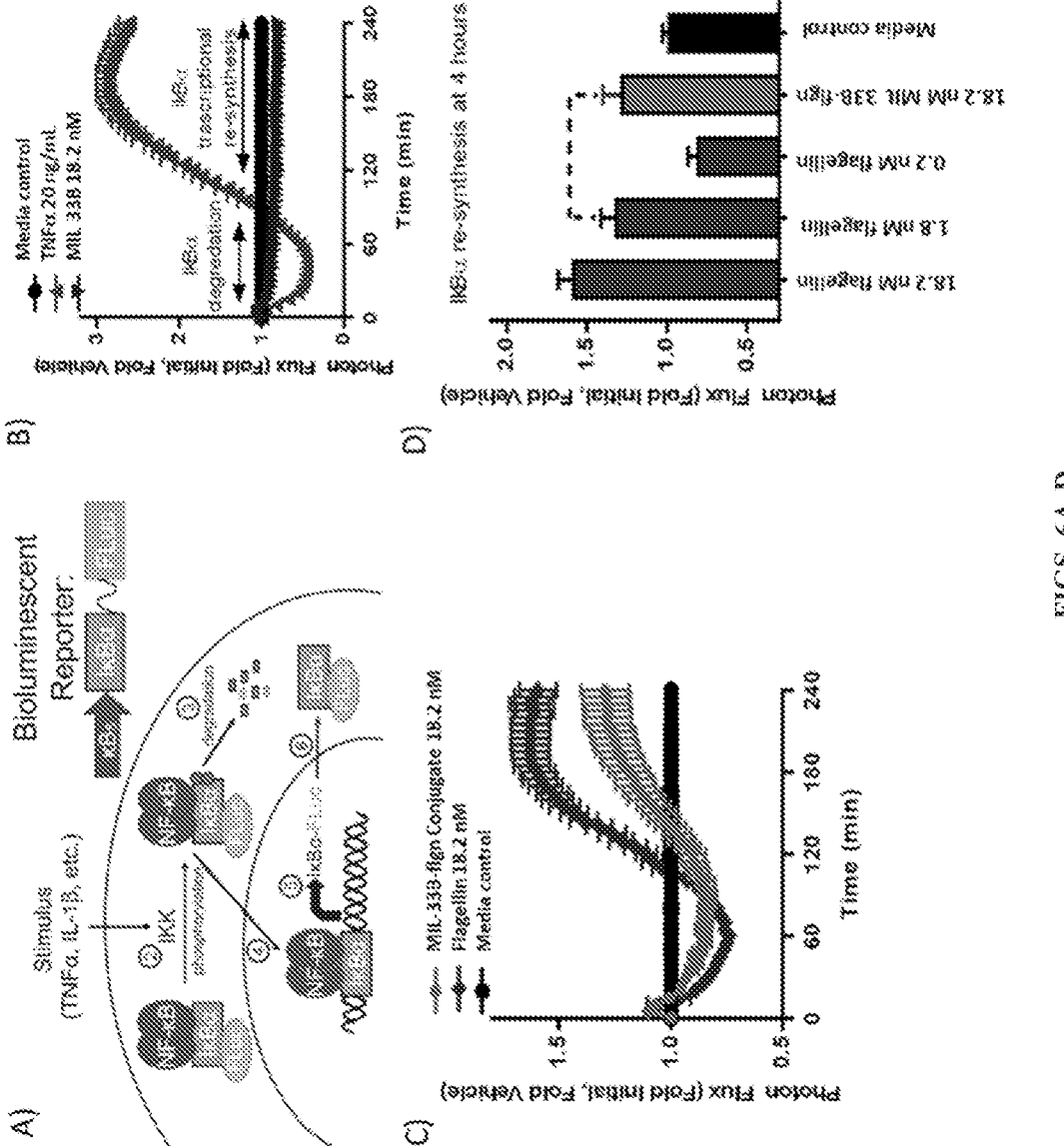
FIGS. 6A-D. Induction of NF-κB by flagellin-conjugated MIL33B.

HCT116 cells, expressing endogenous human 4Ig-B7-H3 and TLR5, the native cognate receptor for flagellin, were stably transduced with a κB-RE₅-IκBα-Fluc reporter. This cell line enables the study of both the activation of IKK through the initial degradation of the IκBα-luciferase (IκBα-Fluc) fusion protein as read out by loss of light production and the subsequent activation of NF-κB transcriptional targets through the re-synthesis of IκBα-Fluc as read out by a secondary increase in light production from the κB response element (RE₅) (FIGS. 6A-B). The MIL33B-flgn conjugate was able to elicit activation of NF-κB via TLR5 at 18.2 nM with a response capacity similar to 1.8 nM of purified flagellin (FIGS. 6C-D). Therefore, MIL33B conjugates can be used for tumor specific-delivery of immune-stimulants to the tumor microenvironment.

Example 6—MIL33B mAb can be Conjugated with DFO and Radiolabeled with ⁸⁹Zr to Detect Tumor Expression of Human 4Ig-B7-H3 Selectively in Syngeneic Animal Tumor Models by PET Imaging MIL33B was radiolabeled with Zr-89 for PET imaging of tumors expressing B7-H3, showing robust signal-to-noise ratios in two different immuno-competent syngeneic murine tumor models.

MIL33B (blue) or IgG2a isotype control (red) antibodies were conjugated with DFO using standard conjugation methods. MIL33B-DFO or IgG2a-DFO were radio-labeled with ⁸⁹Zr by incubating in acetate buffer (pH 7) for 1 hr, and purified through size exclusion chromatography. Labeling was confirmed via radio-TLC.

Immune competent mice bearing subcutaneous 4T1 tumors expressing human 4Ig-B7-H3 or negative vector (see Western blots in FIG. 3) were utilized. 4T1 tumors also have low but detectable levels of murine 2Ig (see Western blots in FIG. 3). Mice were injected i.v. with ~30 μCi of radiolabeled MIL33B antibody or IgG2a control antibody and imaged at 24 and 72 hr post injection on a dedicated small animal PET/SPECT/CT scanner (Albira, Bruker Corp). Similarly, B16F10 cells were transduced with human 4Ig-B7-H3 or empty vector. These cells have less endogenous murine 2Ig-B7H3 than 4T1 tumors. MIL33B was superior, both qualitatively and quantitatively, to isotype control for binding to tumors expressing human 4Ig-B7-H3, and gave the correct rank order of binding for the negative vector as predicted from their low background murine 2Ig-B7-H3 expression levels (FIG. 7).

Example 7—MIL33B mAb Single Agent Treatment Cured Aggressive ICT-Resistant Humanized B16F10 Tumors Administration of MIL33B antibody (i.p.) demonstrated therapeutic potential as a single agent immunotherapeutic in a highly ICT-resistant syngeneic murine breast cancer model.

Murine B16F10 melanoma tumors represent a non-inflammatory "cold" tumor type and are known to be resistant to combination immune checkpoint therapy (ICT) when treated with both anti-PD-1 and anti-CTLA-4. Humanized B16F10 tumors (as indicated above), which were engineered to express endogenous levels of human B7-H3, were implanted subcutaneously in immunocompetent C57B16 mice using 10,000 cells per implantation. Mice were treated on day 3, 6, and 9 post-tumor inoculation with either PBS alone (n=5; i.p.) or 200 μg, 100 μg, and 100 μg/mouse of MIL33B (n=10; i.p.), respectively. Mice were then followed until day 150 post-inoculation. Mice were euthanized when the largest tumor axis was >1.5 cm, there was >3 mm of tumor ulceration, or if the mice were moribund as determined by independent veterinary staff. Overall survival curves and individual tumor growth curves are provided in FIG. 8.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,595,721
U.S. Pat. No. 6,015,542
Ahmed et al., "Humanized Affinity-matured Monoclonal Antibody 8H9 Has Potent Antitumor Activity and Binds to FG Loop of Tumor Antigen B7-H3," J. Biol. Chem., 290:30018-30029.
Barkal et al, "CD24 signalling through macrophage Siglec-10 is a target for cancer immunotherapy," Nature, 572: 392-396, 2019.
Ehrenmann et al., Nucleic Acids Res., 38:D301-D307, 2010.
Ehrenmann & Lefranc, Cold Spring Harbor Protoc., 6:737-749, 2011.
Koenig, "Targeting B7-H3 in cancer," Medicographia, 36:285-292, 2014.
Kairemo, "Radioimmunotherapy of solid cancers: A review," Acta Oncol., 35:343-355, 1996.
Kunik et al., "Structural Consensus among Antibodies Defines the Antigen Binding Site," PLoS Comput Biol., 8(2):e1002388, 2012a.
Kunik et al., "Paratome: An online tool for systematic identification of antigen binding regions in antibodies based on sequence or structure," Nucleic Acids Res., 40(Web Server issue):W521-4, 2012b.
Loo et al., "Development of an Fc-enhanced anti-B7-H3 monoclonal antibody with potent antitumor activity," Clin. Cancer Res., 18:3834-3845, 2012.

Nagase-Zembutsu et al., "Development of DS-5573a: A novel afucosylated mAb directed at B7-H3 with potent antitumor activity," Cancer Sci., 107:674-681, 2016.
Pardoll, "The blockade of immune checkpoints in cancer immunotherapy," Nat. Rev. Cancer, 12:252-264, 2012.
Poty et al, "alpha-Emitters for radiotherapy: From basic radiochemistry to clinical studies-Part 1," J. Nucl. Med., 59:878-884, 2018.
Seaman et al., "Eradication of Tumors through Simultaneous Ablation of CD276/B7-H3-Positive Tumor Cells and Tumor Vasculature," Cancer Cell, 31:501-515, 2017.
Sharma et al., "Novel cancer immunotherapy agents with survival benefit: recent successes and next steps," Nat. Rev. Cancer, 11:805-812, 2011.
Suh et al., "The B7 family member B7-H3 preferentially down-regulates T helper type 1-mediated immune responses," Nat. Immunol., 4:899-906, 2003.
Wang et al., "Blockade of both B7-H4 and CTLA-4 co-signaling pathways enhances mouse islet allograft survival," Islets, 4:284-295, 2012.
Yan et al., "A novel monoclonal antibody against mouse B7-H3 developed in rats," Hybridoma, 31:267-271, 2012.
Zang et al., "B7-H3 and B7x are highly expressed in human prostate cancer and associated with disease spread and poor outcome," Proc. Natl. Acad. Sci. U.S.A., 104:19458-19463, 2007.
Zang et al., "B7x: a widely expressed B7 family member that inhibits T cell activation," Proc. Natl. Acad. Sci. U.S.A., 100:10388-10392, 2003.

What is claimed is:

1. A monoclonal antibody or antibody fragment, wherein the antibody or antibody fragment comprises a heavy chain variable region (VH) comprising VHCDR1, VHCDR2, and VHCDR3 amino acid sequences from SEQ ID NO: 7; and a light chain variable region (VL) comprising VLCDR1, VLCDR2, and VLCDR3 amino acid sequences from SEQ ID NO: 8; and wherein the antibody is capable of binding to B7-H3.

2. The monoclonal antibody or antibody fragment of claim 1, wherein the antibody or antibody fragment comprises;

(a) a heavy chain variable region (VH) having a VHCDR1 amino acid sequence comprising SEQ ID NO: 1, a VHCDR2 amino acid sequence comprising SEQ ID NO: 2, and a VHCDR3 amino acid sequence comprising SEQ ID NO: 3; and a light chain variable region (VL) having a VLCDR1 amino acid sequence comprising SEQ ID NO: 4, a VLCDR2 amino acid sequence comprising SEQ ID NO: 5, and a VLCDR3 amino acid sequence comprising SEQ ID NO: 6;

(b) a heavy chain variable region (VH) having a VHCDR1 amino acid sequence comprising SEQ ID NO: 11, a VHCDR2 amino acid sequence comprising SEQ ID NO: 12, and a VHCDR3 amino acid sequence comprising SEQ ID NO: 13; and a light chain variable region (VL) having a VLCDR1 amino acid sequence comprising SEQ ID NO: 14, a VLCDR2 amino acid sequence comprising SEQ ID NO: 15, and a VLCDR3 amino acid sequence comprising SEQ ID NO: 16;

(c) a heavy chain variable region (VH) having a VHCDR1 amino acid sequence comprising SEQ ID NO: 17, a VHCDR2 amino acid sequence comprising SEQ ID NO: 18, and a VHCDR3 amino acid sequence comprising SEQ ID NO: 19; and a light chain variable region (VL) having a VLCDR1 amino acid sequence comprising SEQ ID NO: 20, a VLCDR2 amino acid sequence comprising SEQ ID NO: 21, and a VLCDR3 amino acid sequence comprising SEQ ID NO: 6; or (d) a heavy chain variable region (VH) having a VHCDR1 amino acid sequence comprising SEQ ID NO: 17, a VHCDR2 amino acid sequence comprising SEQ ID NO: 18, and a VHCDR3 amino acid sequence comprising SEQ ID NO: 19; and a light chain variable region (VL) having a VLCDR1 amino acid sequence comprising SEQ ID NO: 4, a VLCDR2 amino acid sequence comprising SEQ ID NO: 5, and a VLCDR3 amino acid sequence comprising SEQ ID NO: 6.

3. The monoclonal antibody or antibody fragment of claim 1, wherein said antibody or antibody fragment comprises a heavy chain variable sequence having at least 95% identity to SEQ ID NO: 7 and a light chain variable sequence having at least 95% identity to SEQ ID NO: 8.

4. The monoclonal antibody or antibody fragment of claim 1, wherein said antibody or antibody fragment is a humanized antibody.

5. The monoclonal antibody or antibody fragment of claim 1, wherein the antibody fragment is a monovalent scFv (single chain fragment variable) antibody, divalent scFv, Fab fragment, F(ab')$_2$ fragment, Fv fragment, or single chain antibody.

6. The monoclonal antibody or antibody fragment of claim 1, wherein said antibody is a chimeric antibody, bispecific antibody, IgG antibody, or recombinant IgG antibody.

7. The monoclonal antibody or antibody fragment of claim 1, wherein the antibody is conjugated or fused to an imaging agent, a cytotoxic agent, a metal, or a radioactive moiety.

8. The monoclonal antibody or antibody fragment of claim 7, wherein the imaging agent is a fluorophore.

9. The monoclonal antibody or antibody fragment of claim 7, wherein the radioactive moiety is Zr-89, Cu-64, F-18, Y-90, Lu-177, At-211, Ac-225, or Pb-212.

10. The monoclonal antibody or antibody fragment of claim 1, wherein the antibody is an immune conjugate.

11. The monoclonal antibody or antibody fragment of claim 1, wherein the antibody is an antibody-drug conjugate.

12. An isolated nucleic acid encoding the antibody heavy and/or light chain variable region of the antibody molecule of claim 1.

13. An engineered cell comprising a vector comprising a nucleic acid encoding an antibody or antibody fragment of claim 1.

14. A method of making a monoclonal antibody or antibody fragment comprising culturing the engineered cell of claim 13 under conditions that allow expression of the antibody.

15. A pharmaceutical formulation comprising the antibody or antibody fragment of claim 1.

16. A method of treating a patient having a cancer, the method comprising that expresses B7-H3 administering an effective amount of antibody or antibody fragment of claim 1.

17. A method for detecting the presence of B7-H3 on the surface of a cell, in a tissue, in an organ, or an in a biological sample, the method comprising (a) contacting the cell, tissue, organ, or biological sample with an antibody of claim 1; and (b) detecting the presence of the antibody associated with the cell, tissue, organ, or sample.

* * * * *

SEQUENCE LISTING

```
<160> NUMBER OF SEQ ID NOS: 21

<210> SEQ ID NO 1
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 1

Gly Tyr Thr Phe Thr Ser Tyr Val
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 2

Ile Asn Ser Tyr Ser Asp Gly Thr
1               5

<210> SEQ ID NO 3
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 3

Ala Arg Trp Gly Gly Leu Gly Asn Gly Ala Met Asp Tyr
```

-continued

```
1               5                     10

<210> SEQ ID NO 4
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 4

Ser Ser Val Asn Tyr
1               5

<210> SEQ ID NO 5
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 5

Asp Thr Ser
1

<210> SEQ ID NO 6
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 6

Gln Gln Trp Thr Ser Asn Pro Leu Thr
1               5

<210> SEQ ID NO 7
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 7

Glu Val Gln Leu Gln Gln Ser Gly Pro Glu Leu Val Lys Pro Gly Ala
1               5                     10                  15

Ser Val Lys Met Ser Cys Lys Ala Ser Gly Tyr Thr Phe Thr Ser Tyr
            20                  25                  30

Val Met His Trp Val Arg Gln Ser Pro Gly Gln Gly Leu Glu Gly Ile
        35                  40                  45

Gly Tyr Ile Asn Ser Tyr Ser Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Gly Leu Thr Ser Glu Asp Ser Ala Val Tyr Tyr Cys
                85                  90                  95

Ala Arg Trp Gly Gly Leu Gly Asn Gly Ala Met Asp Tyr Trp Gly Gln
            100                 105                 110

Gly Thr Ser Val Thr Val Ser Ser
        115                 120

<210> SEQ ID NO 8
<211> LENGTH: 106
<212> TYPE: PRT
```

```
<213> ORGANISM: Artificial sequence
<220> FEATURE:
<223> OTHER INFORMATION: Synthetic polypeptide

<400> SEQUENCE: 8

Gln Ile Val Leu Thr Gln Ser Pro Ala Ile Met Ser Ala Ser Pro Gly
1               5                   10                  15

Glu Lys Val Thr Met Thr Cys Ser Val Ser Ser Ser Val Asn Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Ala Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Thr Ser Asn Pro Leu Thr
                85                  90                  95

Phe Gly Ala Gly Thr Lys Leu Glu Leu Lys
            100                 105

<210> SEQ ID NO 9
<211> LENGTH: 360
<212> TYPE: DNA
<213> ORGANISM: Artificial sequence
<220> FEATURE:
<223> OTHER INFORMATION: Synthetic polynucleotide

<400> SEQUENCE: 9
gaggtccagc tgcagcagtc tggacctgag ctggtaaagc ctggggcttc agtgaagatg       60
tcctgcaagg cttctggata cacattcact agctatgtca tgcactgggt gaggcagagc      120
cctgggcagg gccttgaggg gattggatat attaattctt acagtgatgg aactaagtac      180
aatgagaagt tcaaaggcaa ggccacactg acttcagaca aatcctccag cacagcctac      240
atggagctca gcggcctgac ctctgaggac tctgcggtct attactgtgc aagatggggga     300 ggattaggaa atggcgctat ggactactgg ggtcaaggaa cctcagtcac cgtctcctca      360

<210> SEQ ID NO 10
<211> LENGTH: 318
<212> TYPE: DNA
<213> ORGANISM: Artificial sequence
<220> FEATURE:
<223> OTHER INFORMATION: Synthetic polynucleotide

<400> SEQUENCE: 10
caaattgttc tcacccagtc tccagcaatc atgtctgcat ctccagggga gaaggtcacc       60
atgacctgca gtgtcagctc aagtgtaaat tacatgcact ggtaccagca gaagtcaggc      120 acctcccca aaagatggat ttatgacaca tccaaactgg cttctggagt ccctgctcgc       180
ttcagtgcca gtgggtctgg gacctcttac tctctcacaa tcagcagcat ggaggctgaa      240
gatgctgcca cttattactg ccagcagtgg actagtaacc cgctcacgtt cggtgctggg      300
accaagctgg agctgaaa                                                     318

<210> SEQ ID NO 11
<211> LENGTH: 9
<212> TYPE: PRT
<213> ORGANISM: Artificial sequence
<220> FEATURE:
<223> OTHER INFORMATION: Synthetic polypeptide
```

```
<400> SEQUENCE: 11

Tyr Thr Phe Thr Ser Tyr Val Met His
1               5

<210> SEQ ID NO 12
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 12

Gly Ile Gly Tyr Ile Asn Ser Tyr Ser Asp Gly Thr Lys Tyr
1               5                   10

<210> SEQ ID NO 13
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 13

Arg Trp Gly Gly Leu Gly Asn Gly Ala Met Asp Tyr
1               5                   10

<210> SEQ ID NO 14
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 14

Ser Ser Val Asn Tyr Met His
1               5

<210> SEQ ID NO 15
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 15

Arg Trp Ile Tyr Asp Thr Ser Lys Leu Ala Ser
1               5                   10

<210> SEQ ID NO 16
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 16

Gln Gln Trp Thr Ser Asn Pro Leu
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 17
```

-continued

```
Gly Tyr Thr Phe Thr Ser Tyr
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 18

Asn Ser Tyr Ser Asp Gly
1               5

<210> SEQ ID NO 19
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 19

Trp Gly Gly Leu Gly Asn Gly Ala Met Asp
1               5                   10

<210> SEQ ID NO 20
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 20

Ser Val Ser Ser Ser Val Asn Tyr Met His
1               5                   10

<210> SEQ ID NO 21
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 21

Asp Thr Ser Lys Leu Ala Ser
1               5
```